US012426813B2

(12) United States Patent
Avirovikj et al.

(10) Patent No.: US 12,426,813 B2
(45) Date of Patent: Sep. 30, 2025

(54) METHODS AND APPARATUS ENABLING COUPLING OF AN ELECTRONICS UNIT TO A BASE UNIT OF A CONTINUOUS ANALYTE MONITORING DEVICE

(71) Applicant: Ascensia Diabetes Care Holdings AG, Basel (CH)

(72) Inventors: Dragan Avirovikj, Stamford, CT (US); Eugene Prais, West Milford, NJ (US); Nicholas Erekovcanski, Butler, NJ (US)

(73) Assignee: Ascensia Diabetes Care Holdings AG, Basel (CH)

( * ) Notice: Subject to any disclaimer, the term of this patent is extended or adjusted under 35 U.S.C. 154(b) by 500 days.

(21) Appl. No.: 17/467,158

(22) Filed: Sep. 3, 2021

(65) Prior Publication Data

US 2022/0071528 A1    Mar. 10, 2022

Related U.S. Application Data

(60) Provisional application No. 63/075,258, filed on Sep. 7, 2020.

(51) Int. Cl.
*A61B 5/145* (2006.01)
*A61B 5/00* (2006.01)

(52) U.S. Cl.
CPC ...... *A61B 5/14546* (2013.01); *A61B 5/14532* (2013.01); *A61B 5/683* (2013.01); *A61B 2562/16* (2013.01); *A61B 2562/225* (2013.01)

(58) Field of Classification Search
CPC ..... A61B 5/0002; A61B 5/002; A61B 5/0024; A61B 45/14503; A61B 5/1451;
(Continued)

(56) References Cited

U.S. PATENT DOCUMENTS 8,333,714 B2    12/2012  Stafford
8,862,198 B2    10/2014  Stafford
(Continued)

FOREIGN PATENT DOCUMENTS

CN     101268932 A    9/2008
CN     100591265 C    2/2010
(Continued)

OTHER PUBLICATIONS

International Search Report of International Application No. PCT/EP2021/074338 mailed Jan. 3, 2022.
(Continued)

*Primary Examiner* — Tse W Chen
*Assistant Examiner* — Alice Ling Zou
(74) *Attorney, Agent, or Firm* — Erise IP, P.A.

(57) ABSTRACT

A coupling tool for coupling together an electronics unit and a base unit of a wearable device for continuous analyte monitoring includes a carrier comprising a receiving feature and a carrier retention device, the carrier retention device configured to retain an electronics unit adjacent the receiving feature. The coupling tool also includes an activator including: a first member at least partially receivable in the receiving feature and a contact member configured to release the electronics unit from the carrier retention device in response to movement of the activator relative to the carrier. The coupling tool is in a locked configuration when the carrier retention device is configured to retain the electronics unit, and the coupling tool is in an unlocked configuration when the carrier retention device is configured to release the electronics unit from the carrier retention device. Other embodiments and methods are also disclosed.

20 Claims, 15 Drawing Sheets

(58) Field of Classification Search
CPC ............ A61B 5/14532; A61B 5/14546; A61B 5/14865; A61B 5/6832–6833; A61B 5/6849; A61B 17/3468; A61B 2560/0412; A61B 2560/0443; A61B 2560/045; A61B 2560/063; A61B 2562/16; A61B 5/103–18; A61B 5/68–6898; A61B 5/1473–14735; A61B 5/1486–14865; A61M 2005/1585

See application file for complete search history.

(56) References Cited

U.S. PATENT DOCUMENTS

| | | | |
|---|---|---|---|
| 9,662,071 | B2 | 5/2017 | Ohkoshi |
| 9,980,670 | B2 | 5/2018 | Funderburk et al. |
| 10,292,632 | B2 | 5/2019 | Lee et al. |
| 2008/0027296 | A1 | 1/2008 | Hadvary et al. |
| 2008/0097246 | A1 | 4/2008 | Stafford et al. |
| 2008/0319414 | A1 | 12/2008 | Yodfat et al. |
| 2009/0257911 | A1 | 10/2009 | Thomas et al. |
| 2010/0198033 | A1 | 8/2010 | Krulevitch et al. |
| 2011/0106126 | A1 | 5/2011 | Love et al. |
| 2011/0191044 | A1 | 8/2011 | Stafford |
| 2011/0288574 | A1 | 11/2011 | Curry et al. |
| 2011/0319729 | A1* | 12/2011 | Donnay ............ A61B 5/14503 600/309 |
| 2012/0157801 | A1 | 6/2012 | Hoss et al. |
| 2012/0197098 | A1 | 8/2012 | Donnay et al. |
| 2013/0150691 | A1 | 6/2013 | Pace et al. |
| 2013/0267811 | A1 | 10/2013 | Pryor et al. |
| 2013/0267813 | A1* | 10/2013 | Pryor ............... A61B 5/14503 600/365 |
| 2014/0066730 | A1 | 3/2014 | Roesicke et al. |
| 2015/0018639 | A1 | 1/2015 | Stafford |
| 2015/0190076 | A1* | 7/2015 | Ohkoshi ............... A61B 5/6849 600/309 |
| 2016/0058344 | A1 | 3/2016 | Peterson et al. |
| 2016/0058474 | A1 | 3/2016 | Peterson et al. |
| 2017/0143243 | A1 | 5/2017 | Deck |
| 2017/0188912 | A1* | 7/2017 | Halac ..................... A61B 5/688 |
| 2017/0202488 | A1 | 7/2017 | Stafford |
| 2017/0245798 | A1 | 8/2017 | Ohkoshi |
| 2018/0116570 | A1 | 5/2018 | Simpson et al. |
| 2018/0116572 | A1 | 5/2018 | Simpson et al. |
| 2018/0325433 | A1 | 11/2018 | Prais et al. |
| 2018/0368774 | A1 | 12/2018 | Gray et al. |
| 2019/0223768 | A1 | 7/2019 | Muller et al. |
| 2020/0009745 | A1 | 1/2020 | Grossard et al. |
| 2020/0100713 | A1 | 4/2020 | Simpson et al. |
| 2020/0170550 | A1 | 6/2020 | Ko et al. |
| 2020/0214633 | A1 | 7/2020 | Antonio et al. |
| 2020/0297257 | A1* | 9/2020 | Konya ............... A61B 5/14865 |
| 2021/0052301 | A1 | 2/2021 | Gass et al. |
| 2021/0052302 | A1 | 2/2021 | Erekovcanski et al. |
| 2021/0169518 | A1* | 6/2021 | Shimizu ............... A61B 5/1473 |

FOREIGN PATENT DOCUMENTS

| | | | |
|---|---|---|---|
| CN | 102065908 | A | 5/2011 |
| CN | 103826528 | A | 5/2014 |
| EP | 2636372 | A1 | 9/2013 |
| EP | 2826422 | A1 | 2/2015 |
| EP | 3170453 | A1 | 5/2017 |
| EP | 3449827 | A1 | 3/2019 |
| JP | 2008506468 | A | 3/2008 |
| JP | 2008508971 | A | 3/2008 |
| JP | 2008246204 | A | 10/2008 |
| JP | 2015509011 | A | 3/2015 |
| JP | 2016087435 | A | 5/2016 |
| TW | 201448360 | | 12/2014 |
| TW | 201719588 | A | 6/2017 |
| WO | 2013035455 | A1 | 3/2013 |
| WO | WO2013090215 | A2 | 6/2013 |
| WO | WO2016036924 | A2 | 3/2016 |
| WO | WO2018027940 | A1 | 2/2018 |
| WO | WO2018195286 | A1 | 10/2018 |
| WO | WO2018206552 | A1 | 11/2018 |
| WO | WO2019054113 | A1 | 3/2019 |
| WO | WO2019176324 | A1 | 9/2019 |

OTHER PUBLICATIONS

U.S. Appl. No. 17/581,842, filed Jan. 21, 2022, Avirovikj et al.
U.S. Appl. No. 17/581,844, filed Jan. 21, 2022, Avirovikj et al.
European Patent Application 21770022.8 Office Action issued Jan. 29, 2024.
Taiwan Patent Application 110132994, Office Action, issued Dec. 3, 2024.
European Patent Application 21770022.8 Intent to Grant issued Jul. 10, 2024.
European Patent Application 24220125.9 Office Action issued Feb. 17, 2025.
Chinese Patent Application 202180054002.7, Office Action, issued Jul. 18, 2025.
Japanese Patent Application 2023-514912, First Office Action, issued Jul. 29, 2024.

\* cited by examiner

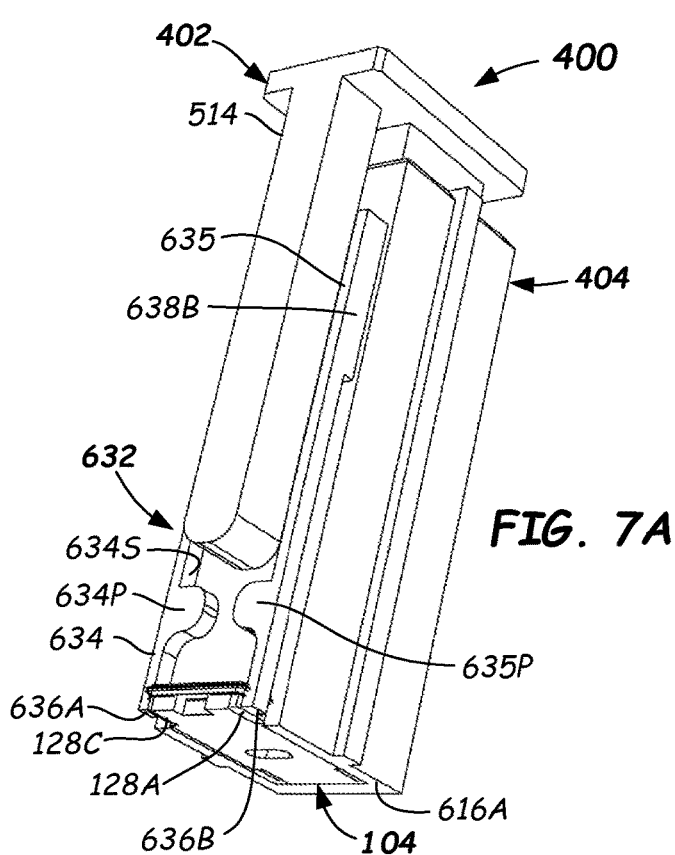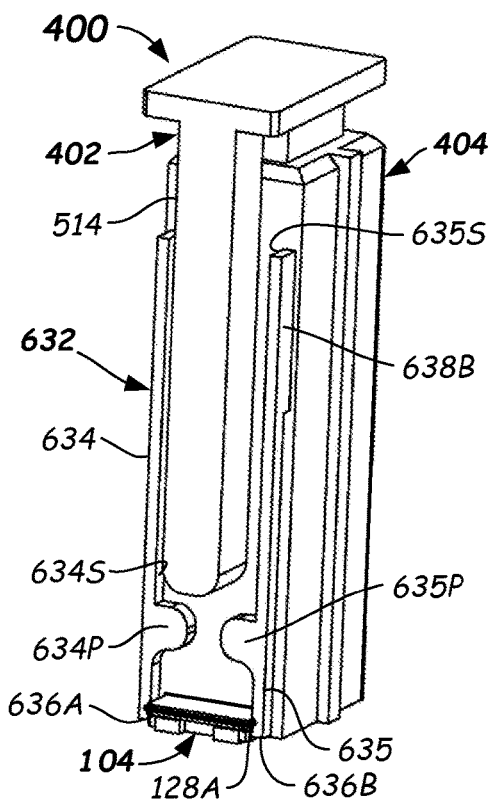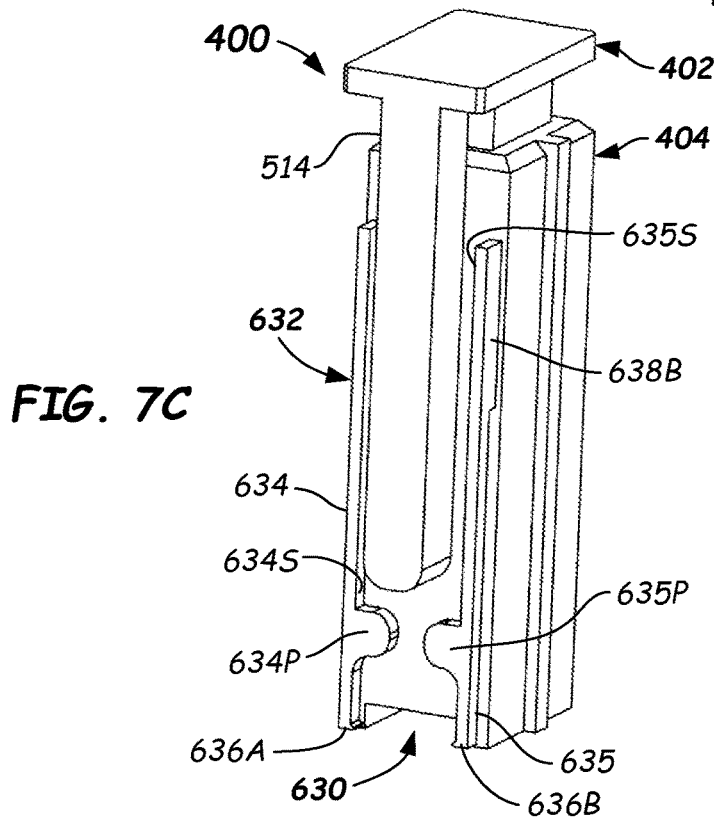

METHODS AND APPARATUS ENABLING COUPLING OF AN ELECTRONICS UNIT TO A BASE UNIT OF A CONTINUOUS ANALYTE MONITORING DEVICE

CROSS REFERENCE TO RELATED APPLICATION

This claims the benefit of U.S. Provisional Patent Application No. 63/075,258, filed Sep. 7, 2020, the disclosure of which is hereby incorporated by reference herein in its entirety for all purposes.

FIELD

Embodiments of the present disclosure relate to methods and apparatus of wearable analyte monitoring devices used during continuous analyte monitoring.

BACKGROUND

Continuous analyte monitoring of an in-vivo sample, such as continuous glucose monitoring (CGM), has become a routine sensing operation, particularly in diabetes care. By providing real-time glucose concentrations, therapeutic and/or clinical actions may be timely applied and the glycemic condition may be better controlled.

During CGM, a biosensor is typically inserted subcutaneously and is continuously operated in an environment surrounded by interstitial fluid. The biosensor provides a signal to a processor or the like within a CGM system that is used to calculate a user's glucose level. These calculations may be made automatically many times throughout the day (e.g., every few minutes or at some other suitable interval).

The CGM system may include a wearable device that adheres to an outer surface of a user's skin. The wearable device may communicate (e.g., wirelessly) with a receiving unit, which may be a hand-held unit carried by the user. The hand-held unit may be a smart phone, for example.

SUMMARY

In some embodiments, a coupling tool for coupling together an electronics unit and a base unit of a wearable device for continuous analyte monitoring is provided. The coupling tool includes: a carrier comprising a receiving feature and a carrier retention device, the carrier retention device configured to retain an electronics unit adjacent the receiving feature; and an activator including a first member at least partially receivable in the receiving feature, and a contact member configured to release the electronics unit from the carrier retention device in response to movement of the activator relative to the carrier. The coupling tool is in a locked configuration when the carrier retention device is configured to retain the electronics unit, and the coupling tool is in an unlocked configuration when the carrier retention device is configured to release the electronics unit from the carrier retention device.

In some embodiments, a method of coupling an electronics unit to a base unit of a wearable device of a continuous analyte monitoring system is provided. The method includes: retaining the electronics unit to a carrier of a coupling tool by use of a carrier retention device; positioning the electronics unit adjacent the base unit; and engaging the carrier retention device with an activator of the coupling tool, wherein the engaging releases the electronics unit from the carrier retention device.

In some embodiments, a coupling tool is provided. The coupling tool includes: a carrier comprising a receiving feature; a carrier retention device attached to the carrier, the carrier retention device comprising a first arm and a second arm configured to retain an electronics unit adjacent the receiving feature; and an activator including: a first member at least partially receivable in the receiving feature and configured to contact the electronics unit in response to the coupling tool being in an unlocked configuration; and a contact member configured to release the electronics unit from the carrier retention device in response to the coupling tool being in the unlocked configuration and to couple the electronics unit to a base unit of a wearable device of a continuous analyte monitor.

Other features, aspects, and advantages of embodiments in accordance with the present disclosure will become more fully apparent from the following detailed description, the claims, and the accompanying drawings by illustrating a number of example embodiments. Various embodiments in accordance with the present disclosure may also be capable of other and different applications, and its several details may be modified in various respects, all without departing from the scope of the claims. Accordingly, the drawings and descriptions are to be regarded as illustrative in nature, and not as restrictive. The drawings are not necessarily drawn to scale.

BRIEF DESCRIPTION OF THE DRAWINGS

FIG. 7A illustrates a bottom isometric view of an assembly of a carrier and an activator of a coupling tool used to couple an electronics unit to a base unit of a wearable device for use during continuous analyte monitoring, wherein the coupling tool is shown retaining an electronics unit and the activator is received in the carrier in accordance with embodiments provided herein.

FIG. 7B illustrates a top isometric view of the coupling tool including a carrier and activator of FIG. 7A in accordance with embodiments provided herein.

FIG. 7C illustrates a top isometric view of the carrier of FIG. 7A with an activator received in the carrier but without an electronics unit retained by the coupling tool in accordance with embodiments provided herein.

DETAILED DESCRIPTION

Figure 1A:
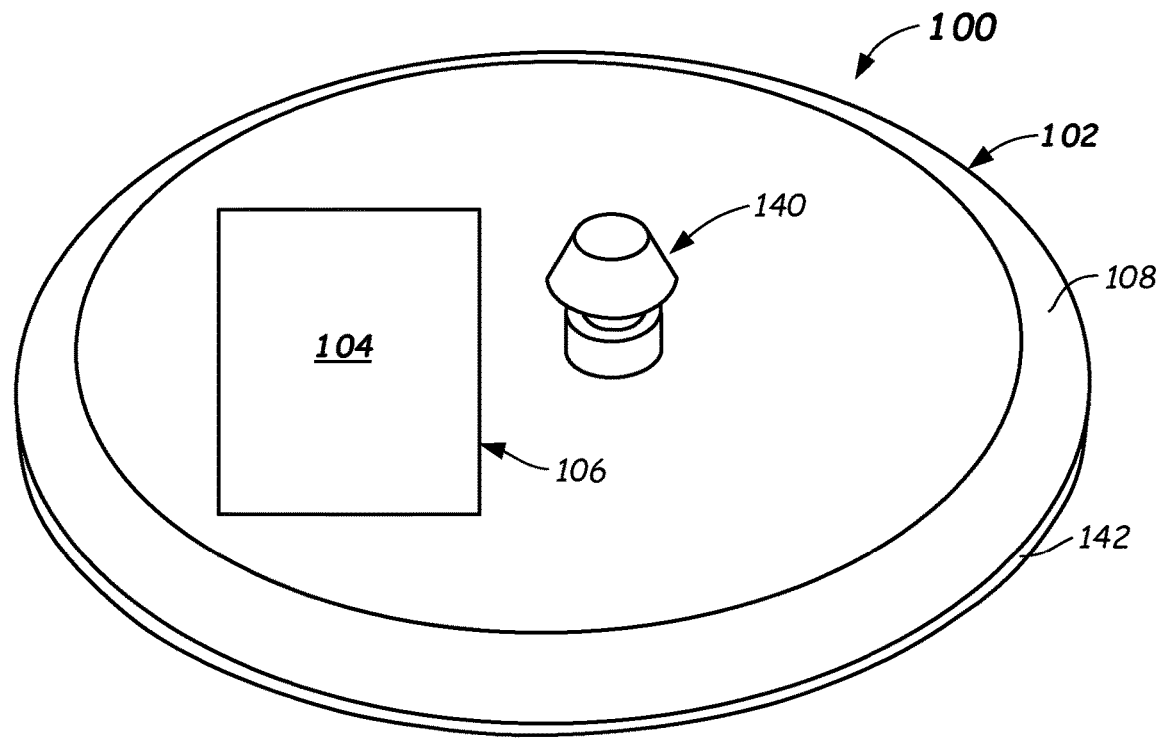
FIGS. 1A and 1B illustrate a top isometric view and a side elevation view, respectively, of a wearable device for use during continuous analyte monitoring in accordance with embodiments provided herein.

In order to more closely monitor a person's analyte level (e.g., glucose concentration) and detect changes in the analyte level, methods and apparatus for continuous analyte monitoring (e.g., continuous glucose monitoring (CGM)) have been developed. While CGM systems generate glucose signals "continuously" during operation, such as continuous electrochemical signals, measurements of the generated glucose signals are typically performed every few minutes, rather than being truly continuous. While the description below is related to continuous glucose monitoring, the apparatus and methods described below may be readily adapted to monitoring of other analytes in other continuous analyte monitoring systems, such as, e.g., cholesterol, lactate, uric acid, alcohol, or the like.

CGM systems generally have a wearable portion (a "wearable device") that communicates wirelessly with an external device, such as a hand-held monitor or another portable device such as a cell phone, a computer, or a server. The wearable device may be worn for several days or even several weeks (e.g., 1-2 weeks) before being removed and replaced. The wearable device includes a biosensor that is inserted (implanted) subcutaneously. The wearable device may also include circuitry coupled to the biosensor that is configured to bias the biosensor and measure current signals generated by an electrochemical reaction with components of the implanted biosensor. The wearable device may also include processing circuitry for determining analyte (e.g., glucose) levels based on measured current signals, as well as electronic transmitter circuitry for communicating analyte (e.g., glucose) levels to an external device. The wearable device may be attached (e.g., adhered) to the outer surface of the skin, such as to the abdomen, the back of the upper arm, or another suitable location. CGM systems measure analyte (e.g., glucose) concentrations or analyte levels in interstitial fluid or in samples of non-direct capillary blood.

CGM systems may provide frequent measurements of a user's analyte (e.g., glucose) levels without the need for each such measurement to be accompanied by the drawing of a blood sample, such as by finger sticks. CGM systems may still employ an occasional finger stick and the use of a blood glucose measuring (BGM) system, such as the Contour NEXT One® by Ascensia Diabetes Care AG of Basel Switzerland, for checking calibration of the CGM system.

As described above, the wearable device of a CGM system is generally worn for a period of time, and then is removed and replaced with a new wearable device. Having to replace the wearable device of a CGM system after a designed interval can significantly increase the costs of performing such continuous analyte monitoring.

In embodiments described herein, a wearable device may include a base unit (e.g., a disposable portion) and an electronics unit (e.g., a reusable portion). In some embodiments, the base unit may include a power source for the wearable device, an analyte sensor (biosensor), and/or other electronic components. The electronics unit may include electronic circuitry used, for example, to provide a bias voltage to the analyte sensor, and to measure current signals through the analyte sensor, and may also compute analyte concentration values, such as glucose concentration values, based on the measured current signals, and/or transmit the analyte concentration value information to an external device.

In some embodiments, the electronics unit may include a power supply for the wearable device. Example circuitry within the electronics unit may also include an analog front end for biasing the analyte sensor and for sensing current that passes through the analyte sensor, such as operational amplifiers, current sensing circuitry, etc. Other circuitry within the electronics unit may include processing circuitry such as analog-to-digital converters (ADCs) for digitizing current signals, memory for storing digitized current signals, a controller such as microprocessor, microcontroller or the like for computing glucose concentration values based on measured current signals, and transmitter/receiver circuitry for transmitting glucose concentration values to an external device and/or receiving instructions from the external device.

The electronics unit is generally the most expensive portion of the wearable device and can last significantly longer than the period in which the wearable device is employed. For example, wearable devices are typically discarded after about two weeks, while the electronics unit may be reused with 10, 20, 50, 100 or even more base units.

The wearable device may be very small so as not to interfere with movement of the user or irritate the user. Thus, the electronics unit may be small, which may make manually coupling the electronics unit and the base unit together difficult. As such, a coupling tool and methods of coupling a reusable electronic unit to a base unit are provided. These and other embodiments are described below with reference to FIGS. 1A-11.

Figure 1B:
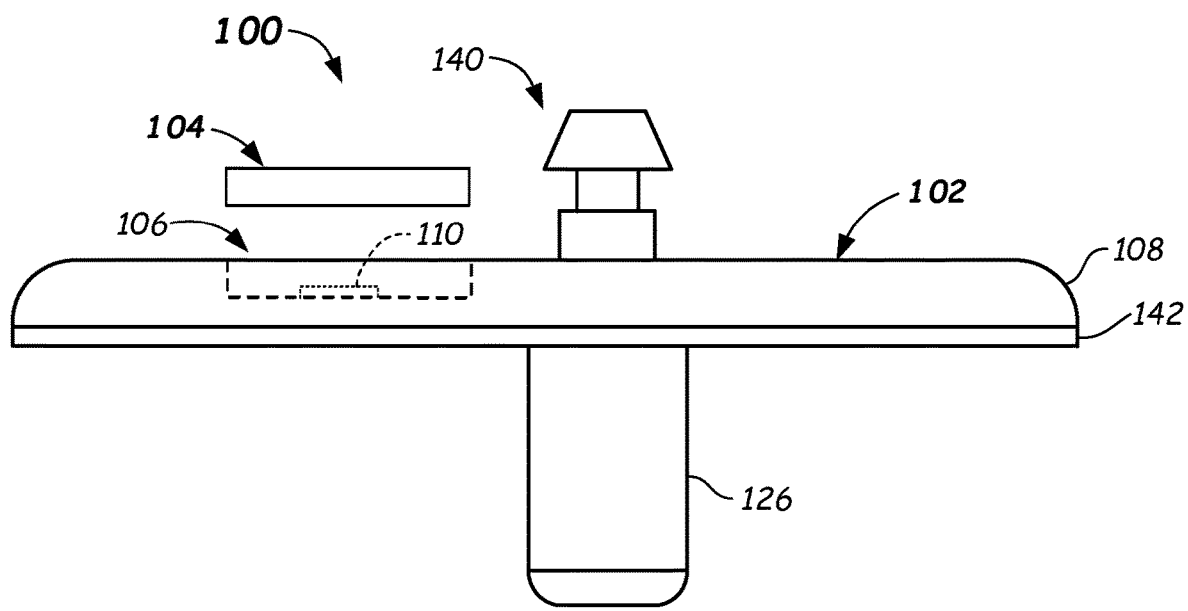
Figure 1C:
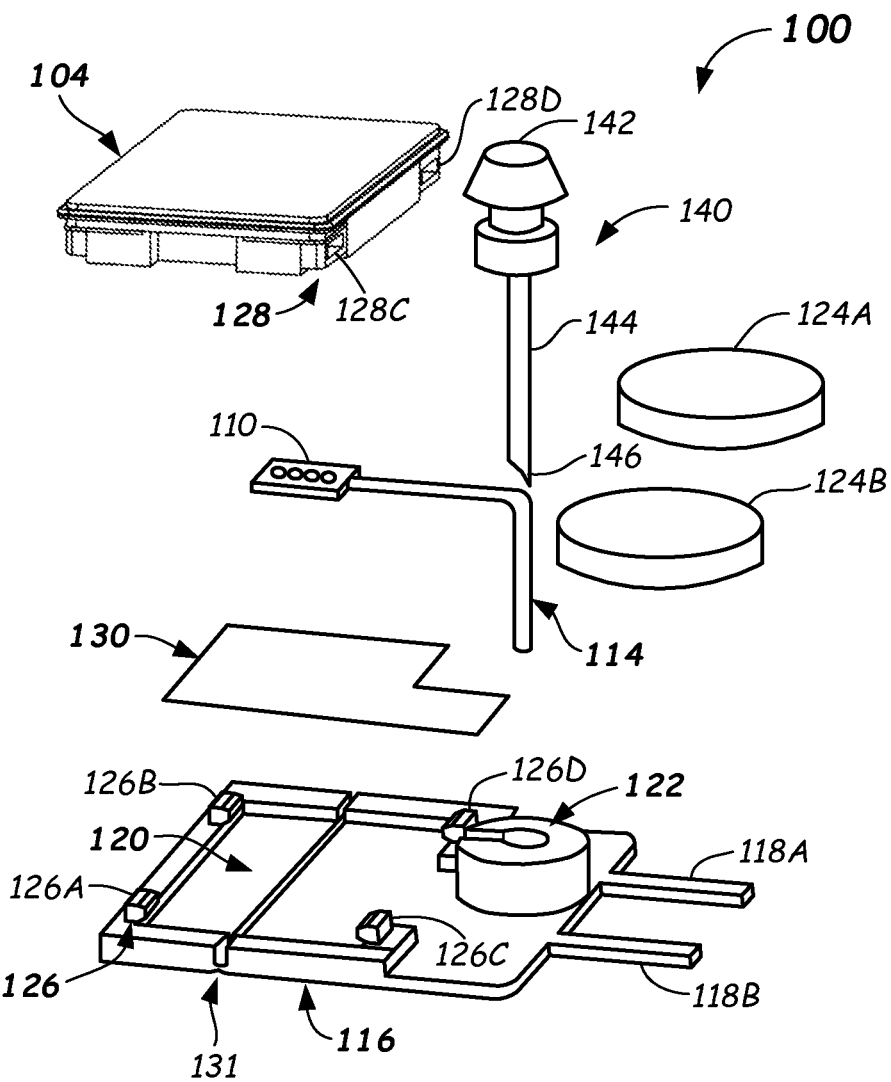
FIG. 1C illustrates an exploded isometric view of an example embodiment showing some components making up a wearable device for use during continuous analyte monitoring in accordance with embodiments provided herein.
Figure 1D:
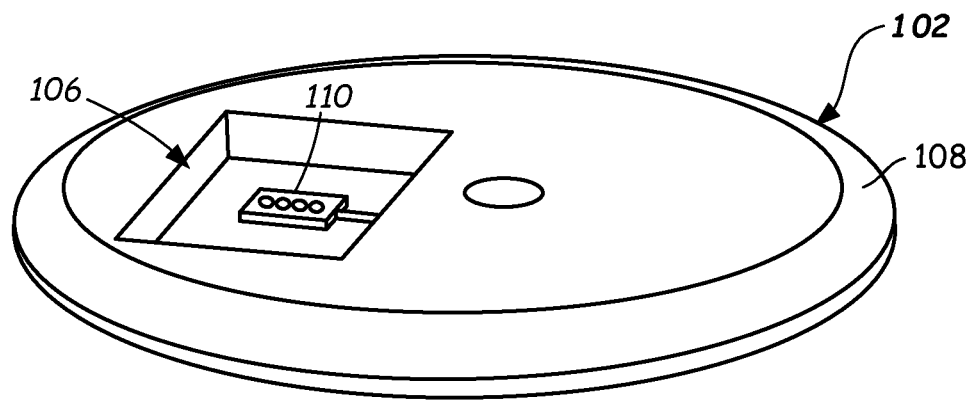
FIG. 1D illustrates an isometric view of a base unit of a wearable device without an electronics unit coupled thereto in accordance with embodiments provided herein.
Figure 1E:
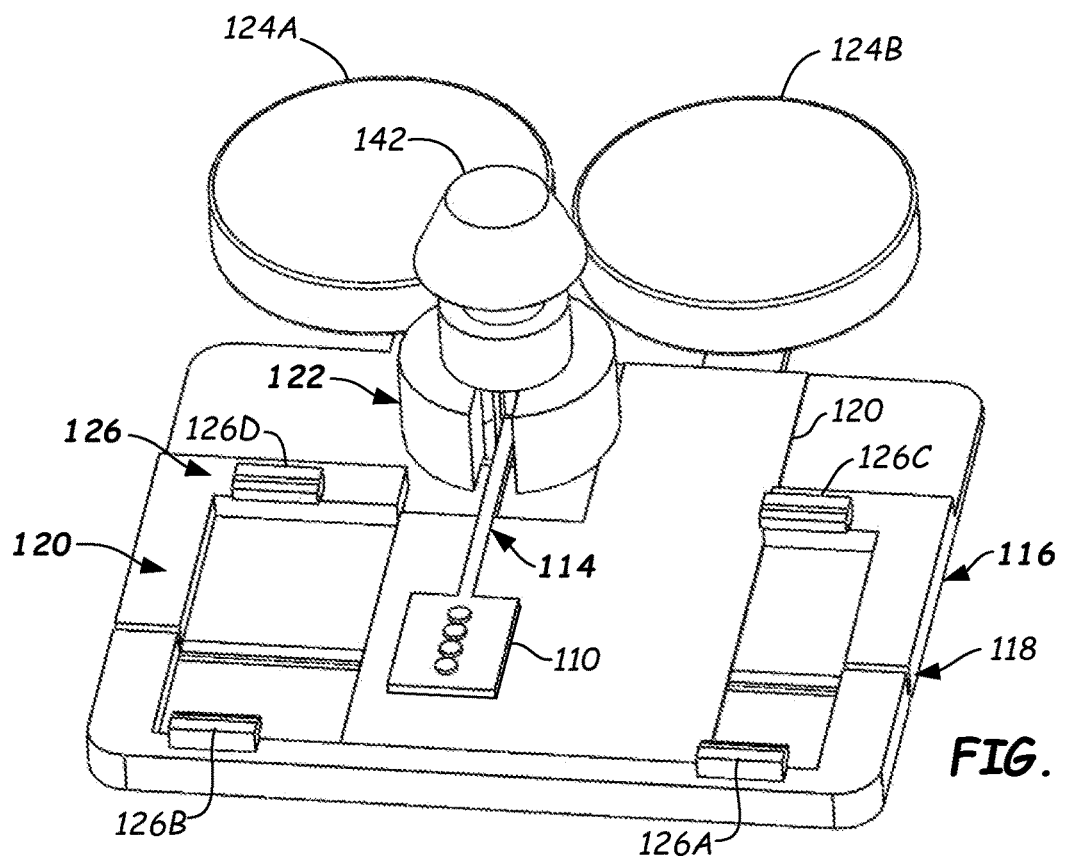
FIG. 1E illustrates an enlarged isometric view of a base structure of the base unit of FIG. 1C in accordance with embodiments provided herein.
Figure 1F:
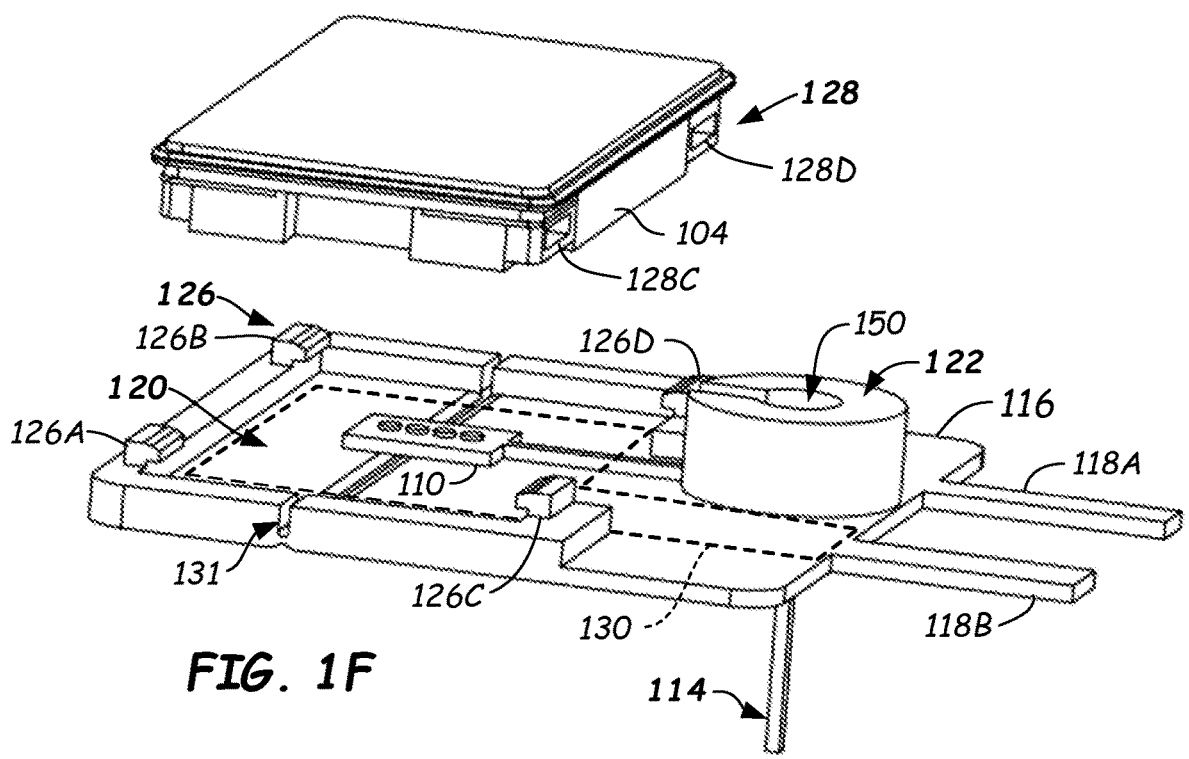
FIG. 1F illustrates an enlarged isometric, partially exploded view of a base structure of a base unit and an electronics unit of FIG. 1C with the electronics unit positioned above the base structure in accordance with embodiments provided herein.
Figure 1G:
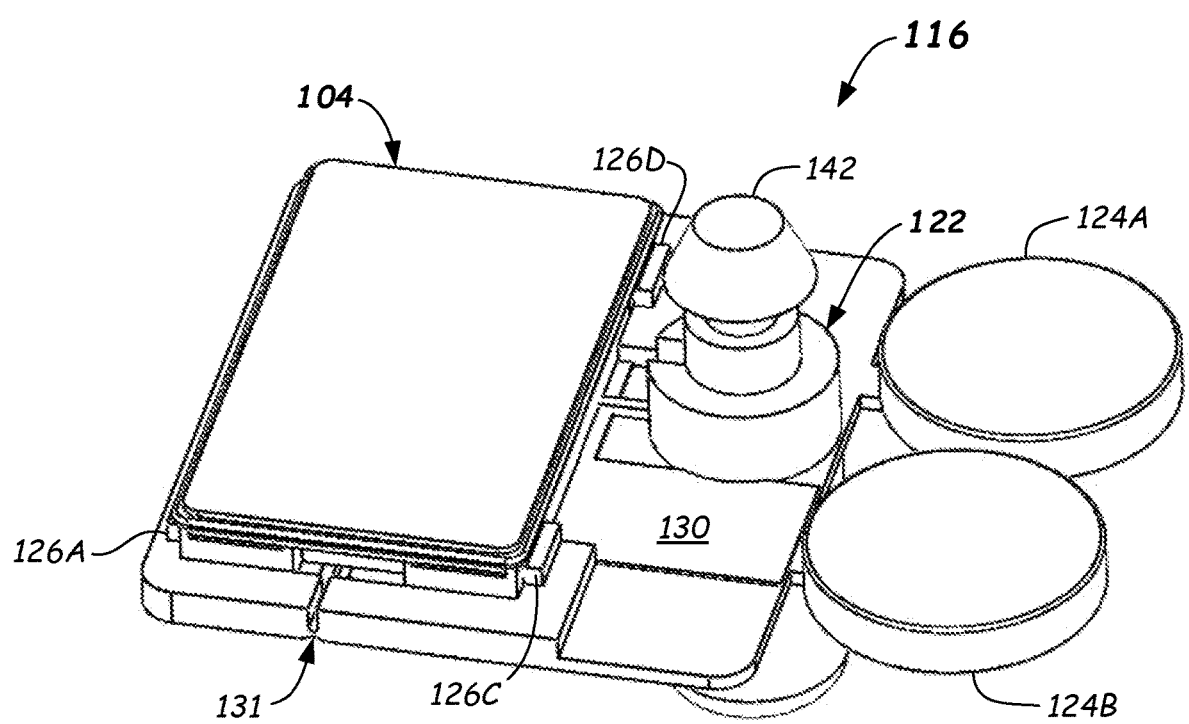
FIG. 1G illustrates a top isometric view of another embodiment of a base unit and an electronics unit with the electronics unit positioned within a base structure of the base unit in accordance with embodiments provided herein.

Reference is now made to FIGS. 1A-1H, which illustrate various views of a wearable device 100 and components thereof for use during continuous analyte monitoring. FIGS. 1A-1B illustrate wearable device 100 in accordance with embodiments provided herein. FIG. 1C illustrates an exploded isometric view of an example embodiment of components located within the wearable device 100. FIG. 1D illustrates an isometric view of a base unit 102 of the wearable device 100 without an electronics unit located therein. The components of FIG. 1C may be located within the base unit 102 of FIG. 1D, which may be overmolded, for example, to retain the components. FIGS. 1E-1H illustrate various isometric views of examples of base structures included in the base unit 102.

The wearable device 100 may include the base unit 102 (e.g., a disposable base unit) and an electronics unit 104 (e.g., a reusable electronics unit) that interface and couple with each other to form the wearable device 100. The electronics unit 104 is sometimes referred to as a transmitter unit. The base unit 102 may include a cavity or opening 106 or other coupling structure that receives the electronics unit 104. Apparatus and methods are disclosed herein that enable a user to couple the electronics unit 104 to the base unit 102. In some embodiments, the base unit 102 is configured to be disposed of after a single analyte monitoring period (e.g., 7 days, 10 days, 14 days, or some other time period), while the electronics unit 104 is configured to be removed from the base unit 102 after the single analyte monitoring period and re-used with another base unit. For example, the electronics unit 104 may be re-used with 2, 5, 10, 50, 100 or more new base units.

In some embodiments, the base unit 102 is sealed. For example, an encapsulation layer 108 may be formed over the components within the base unit 102. In some embodiments, the encapsulation layer 108 may include the opening 106 that allows the electronics unit 104 to be coupled to the base unit 102. In some embodiments, the encapsulation layer 108 creates a waterproof seal around the base unit 102 and its internal components. A connector 110 may remain exposed, such as in opening 106, so a connector on the electronics unit 104 may make an electrical connection with the connector 110. The encapsulation layer 108 may be formed from a single layer or multiple layers. For example, the encapsulation layer 108 may be formed from one or more layers of liquid silicone rubber (LSR), a thermoplastic elastomer (TPE), or the like. Other suitable sealing materials may be used.

The base unit 102 may include an analyte sensor 114 (FIG. 1C) that is electrically coupled to the connector 110 and which is operable to generate electrical signals in response to contact and reaction with interstitial fluid. The electrical signals may be transmitted to the electronics unit 104 where the electrical signals are measured. The electronics unit 104 or an external device (not shown) may determine a glucose concentration (or concentration of another analyte) based at least in part on the measured electrical signals.

FIGS. 1C and 1E-1H illustrate exploded and other isometric views of example embodiments of some components that may be located within the base unit 102 of the wearable device 100, including the electronics unit 104. As shown, the base unit 102 may include a base structure 116 that may be a chassis or the like that retains components within the base unit 102. Some embodiments of base structure 116 may have one or more power source support locations 118A-118B, an electronics unit support location 120, and a sensor assembly support location 122. In some embodiments, the base structure 116 may be formed from a plastic, for example, such as, but not limited to, acrylonitrile butadiene styrene (ABS), polycarbonate, nylon, acetal, polyphthalamide (PPA), polysulfone, polyethersulfone, polyetheretherketone (PEEK), polypropylene, high-density polyethylene (HDPE), and low-density polyethelene (LDPE). Other suitable materials may be used.

The power source support locations 118A, 118B provide locations for supporting one or more power sources 124A, 124B used to supply electrical power to components of the wearable device 100 such as to the electronics unit 104. For example, one or more power sources 124A, 124B may be positioned at the power source support locations 118A, 118B. In some embodiments, the one or more power sources 124A, 124B may be batteries, storage capacitors, solar cells, a generator, or the like. While the power sources 124A, 124B are shown as being two batteries, it will be understood that fewer, more and/or different power sources may be used. The power source support locations 118A, 118B may be any suitable shape (e.g., rectangular, square, round, etc.) to receive the one or more power sources 124A, 124B. In some embodiments, the power sources 124A, 124B may be located in the electronics unit 104.

The electronics unit support location 120 is configured to retain the electronics unit 104 coupled or otherwise attached to the base unit 102. In some embodiments, the electronics unit support location 120 may include one or more first retention features 126. In some embodiments, the electronics unit support location 120 may include four first retention features 126, which are referred to individually as first retention features 126A-126D. The first retention features 126 may interface with and/or press against second retention features 128, referred to individually as second retention features 128A-128D, on the electronics unit 104 to couple and retain the electronics unit 104 to the base structure 116 of the base unit 102, as shown for example in FIG. 1G. Fewer, more, and/or different retention features may be used to secure the electronics unit 104 to the base structure 116. The first retention features 126 may include, for example, projections that engage openings of the second retention features 128 in the electronics unit 104. In some embodiments, the first and second retention features 126, 128 may include magnets, Velcro, surfaces with adhesives, or the like.

In some embodiments, the electronics unit support location 120 may include a break location 131 (FIGS. 1C, 1F, and 1G), such as a channel, groove, scribe line, or the like, that allows base structure 116 to bend and/or break such that the first retention features 126 disconnect and/or release the electronics unit 104 when the electronics unit 104 is to be removed from the base unit 102 and/or the base structure 116. Other release and/or break locations may be used. In some embodiments, other retention features may be used to retain the electronics unit 104 wherein the other retention features do not require bending of the base structure 116 to remove the electronics unit 104.

A substrate 130, such as a circuit board, a flexible circuit board, etc., may be located within the electronics unit support location 120 and may include the connector 110 that provides an electrical interface to a similar connector (not shown) on the electronics unit 104. For example, the connector 110 may be electrically connected to the power sources 124A, 124B by conductors (not shown) so as to allow the power sources 124A, 124B to provide electrical power to the electronics unit 104 when the electronics unit 104 is positioned within the electronics unit support location 120. The connector 110 may also be electrically connected to the analyte sensor 114 to provide a voltage to the analyte sensor 114.

Figure 1H:
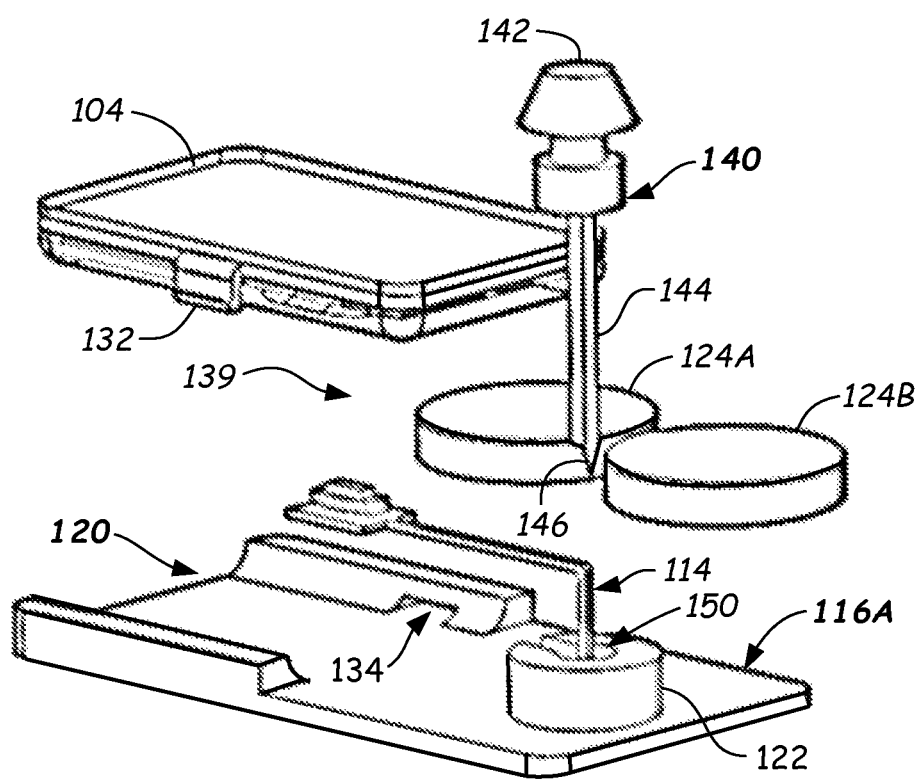
FIG. 1H illustrates an exploded view of an alternative embodiment of a base structure and an electronics unit in accordance with embodiments provided herein.

FIG. 1H illustrates an exploded isometric view of another alternative embodiment of a base structure 116A and the electronics unit 104 of FIG. 1C with other examples of first and second retention features 132, 134 that retain the electronics unit 104 within the base structure 116A. In the embodiment of FIG. 1H, the electronics unit 104 has first retention features 132 and the base structure 116A has second retention features 134. The first retention features 132 on the electronics unit 104 may extend into the second retention features 134 on the base structure 116A, which are openings that are configured to receive the first retention features 132.

The sensor assembly support location 122 provides a mounting location for at least a portion of an analyte sensor assembly 139 that may include an insertion device 140 and an insertion device cap 142, for example. The insertion device 140 may include an insertion portion 144 including a sharpened end 146 (FIG. 1C) that pierces skin to introduce the analyte sensor 114 into a subcutaneous region of a user as described herein. The insertion portion 144 also may be referred to as an insertion shaft, needle, trocar, sharp, or the like.

The insertion portion 144 of the insertion device 140 may be made, for example, from a metal such as stainless steel, or a non-metal such as plastic. Other materials may be used. In some embodiments, the insertion portion 144 of the insertion device 140 may be, but is not limited to, a round C-channel tube, a round U-channel tube, a stamped sheet metal part folded into a square U-profile, a molded/cast, laser cut or machined metal part with a U-channel profile, or a solid metal cylinder with an etched or ground square U-channel. Other insertion portion shapes may be used. The channel formed in the insertion portion 144 carries the analyte sensor 114 during insertion. In some embodiments, portions of the insertion device 140 may be formed from a plastic, such as, but not limited to, ABS, polycarbonate, nylon, acetal, PPA, polysulfone, polyethersulfone, PEEK, polypropylene, HDPE, LDPE, etc. Other materials may be used.

The insertion portion 144 may extend through a sensor opening 150 (FIG. 1F) in the sensor assembly support location 122 of the base structure 116, 116A, for example. The analyte sensor 114 is electrically connected to the connector 110 of the substrate 130 within the electronics unit support location 120. The connector 110 electrically connects the analyte sensor 114 to the electronics unit 104 positioned within the electronics unit support location 120.

The first and second retention features 126, 128, 132, 134 described herein secure (e.g., couple) the electronics unit 104 to the base structure 116, 116A of the base unit 102 during continuous analyte monitoring, while allowing the electronics unit 104 to be removed and reused after a continuous analyte monitoring period. The base unit 102 may be configured to be disposed of after a single analyte monitoring period, while the electronics unit 104 may be configured to be separated from the base unit 102 after the single analyte monitoring period and re-used with other base units. For example, the base structure 116 may be bent along the break location 131, which releases the first retention features 126 (FIG. 1F) from the electronics unit 104. In some embodiments, the single analyte monitoring period may be at least 7 to 10 days (and, e.g., up to 14 days or longer). The electronics unit 104 may be removed from the base unit 102 and reused (e.g., 5, 10, 20, 50, 100 or more times, each time with a new base unit 102 that includes a new analyte sensor 114).

Figure 2:
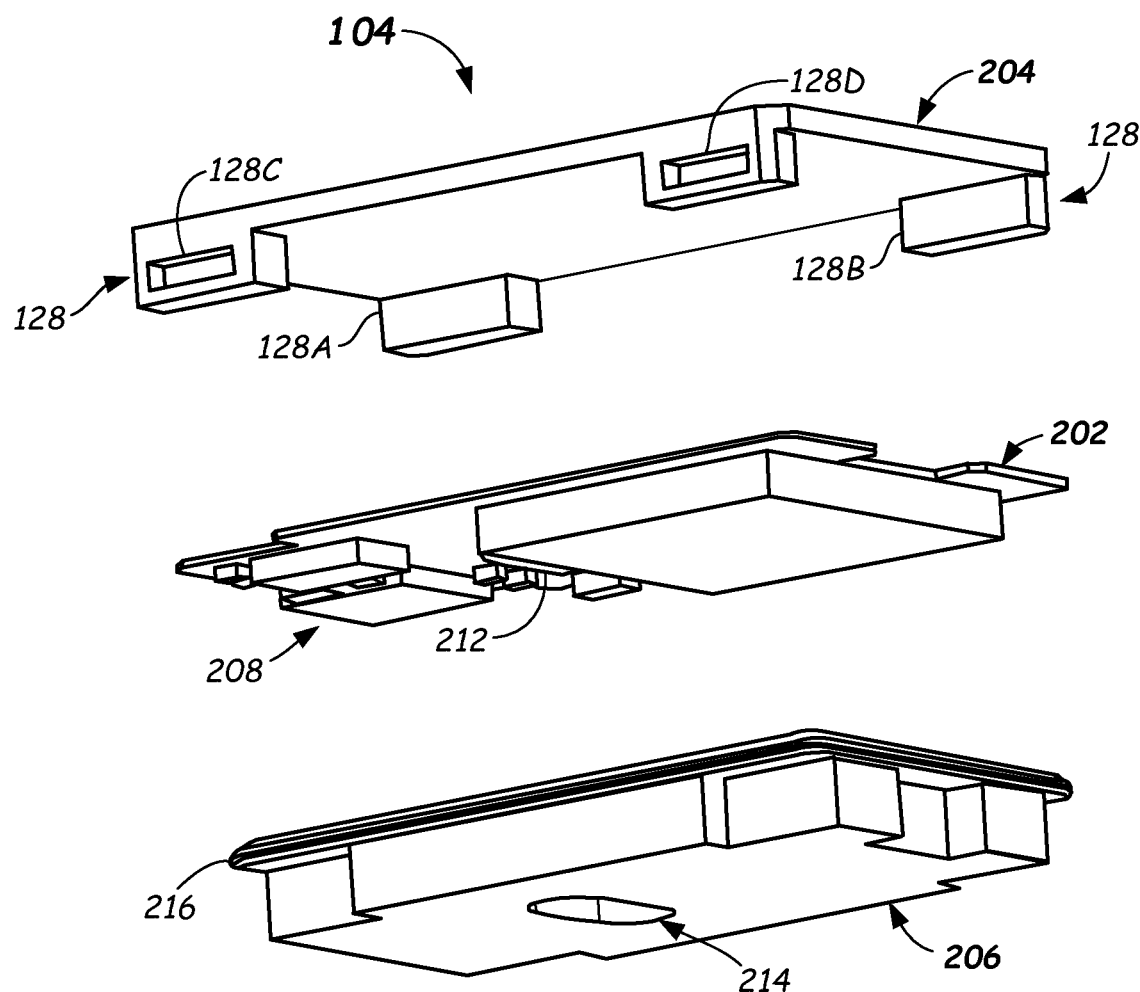
FIG. 2 illustrates an exploded view of an electronics unit of a wearable device for use during continuous analyte monitoring in accordance with embodiments provided herein.

FIG. 2 illustrates an exploded view of an example of the electronics unit 104 according to some embodiments provided herein. In the embodiment of FIG. 2, the electronics unit 104 may include a substrate 202 that couples to a top cover 204 and can be covered by a bottom cover 206 (e.g., an overmold portion) to cover and seal the substrate 202 and any components 208 thereon. The substrate 202 may be a circuit board, a flexible circuit board, or another mounting location for electronic circuitry used within the electronics unit 104. The top cover 204 and/or the bottom cover 206 may be formed from one or more layers of liquid silicone rubber (LSR), a thermoplastic elastomer (TPE), a molded plastic cover, or the like. Other materials may be used such as, but not limited to, ABS, polycarbonate, nylon, acetal, PPA, polysulfone, polyethersulfone, PEEK, polypropylene, HDPE, LDPE, etc.

The substrate 202 may include an interface 212 (e.g., a connector) configured to interface with the connector 110 (FIG. 1C) of the base unit 102 when the electronics unit 104 is positioned within the electronics unit support location 120 of the base structure 116. An opening 214 in bottom cover 206 may be provided to allow the interface 212 to couple with the connector 110 of the base unit 102, for example. In some embodiments, one or more of the components 208 may electrically couple to the analyte sensor 114 through the interface 212 and the connector 110 of the base unit 102.

In some embodiments, the bottom cover 206 may include a sealing member 216, such as a lip or similar feature, configured to seal against a sidewall or other portion of the opening 106 of the base unit 102 (see also FIGS. 3A and 3B below), such that the electronics unit 104 and the base unit 102 form a sealed unit when the electronics unit 104 is positioned within the base unit 102. In some embodiments, the top cover 204 may include the one or more second retention features 128 configured to interface with first retention features 126A-126D (FIG. 1C) within the electronics unit support location 120 (e.g., one or more of first retention features 126, for example). Such first and second retention features may interface to hold the electronics unit 104 securely to the base unit 102 and keep the connector 110 in contact with the interface 212 during use. In other embodiments, the top cover 204 may include a sealing member and/or the bottom cover 206 may include retention features.

Figure 3A:
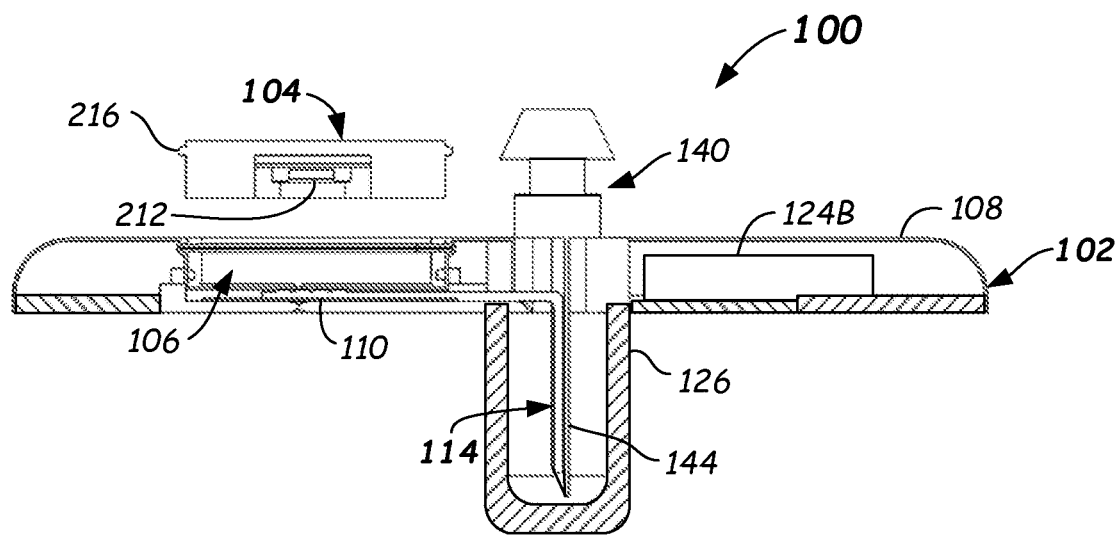
FIG. 3A illustrates a cross-sectioned side view of a wearable device for use during continuous analyte monitoring showing an electronics unit removed from a base unit in accordance with embodiments provided herein.
Figure 3B:
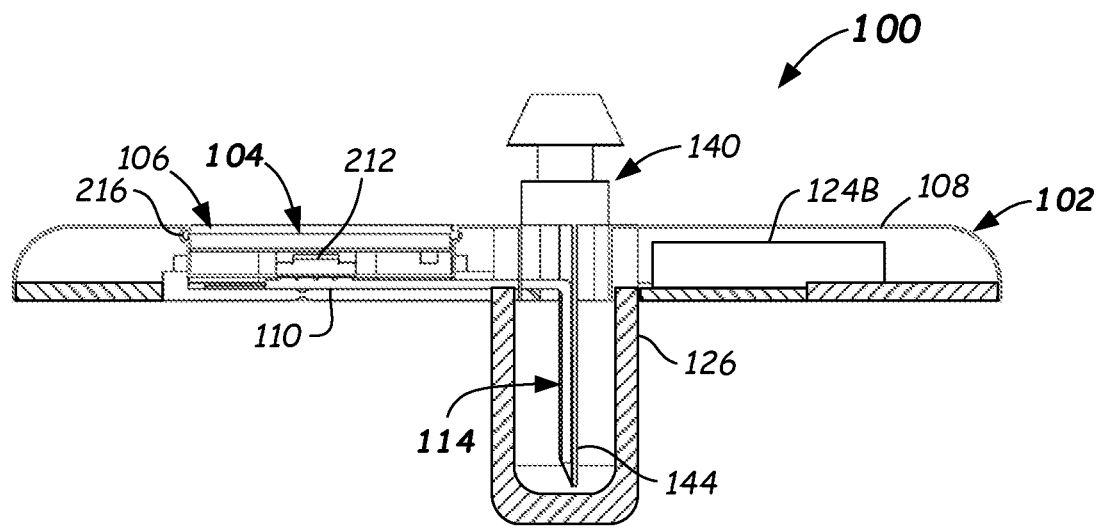
FIG. 3B illustrates a cross-sectioned side view of the wearable device of FIG. 3A with the electronics unit and the base unit coupled together in accordance with embodiments provided herein.

FIG. 3A illustrates a cross-sectioned view of the wearable device 100 with the electronics unit 104 removed from the base unit 102 in accordance with some embodiments. FIG. 3B illustrates a cross-sectioned view of the wearable device 100 of FIG. 3A with the electronics unit 104 and the base unit 102 coupled together in accordance with some embodiments. As described herein, both the electronics unit 104 and the base unit 102 may be sealed units (e.g., waterproof), with only the interface 212 of the electronics unit 104 and the connector 110 of the base unit 102 exposed. When the electronics unit 104 is coupled with the base unit 102, the connector 110 and the interface 212 may also be sealed from any external environment.

Figure 4A:
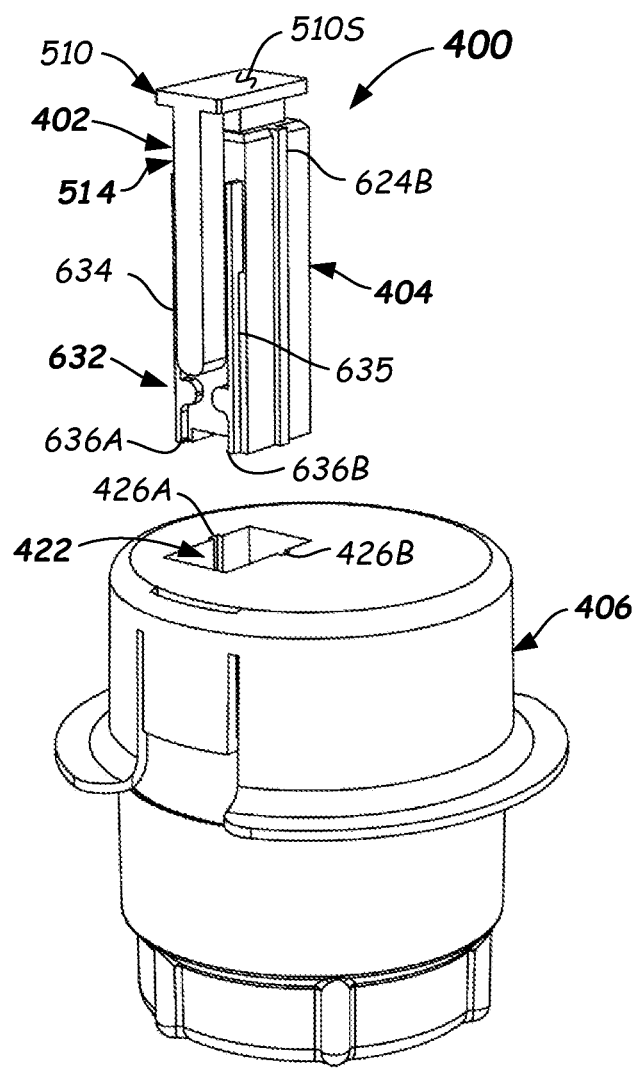
FIG. 4A illustrates a top isometric view of a coupling tool used to couple an electronics unit to a base unit of a wearable device for use during continuous analyte monitoring and an inserter used to attach the wearable device to a user in accordance with embodiments provided herein.

Reference is now made to FIG. 4A, which illustrates a side isometric view of a coupling tool 400 that may be used to couple the electronics unit 104 (FIG. 1B) to the base unit 102 of the wearable device 100 (FIG. 1B). The coupling tool 400 may be used to couple together other electronics units and base units of other types of wearable devices. The coupling tool 400 includes and is made up of an activator 402 and a carrier 404. The coupling tool 400 may be used with an inserter 406 that enables a user to attach the wearable device 100 to the user as described herein. In summary, the base unit 102, without the electronics unit 104 coupled thereto, may be retained within the inserter 406 (see FIG. 8A). The electronics unit 104 is retained and held by the carrier 404, and the carrier 404 and the electronics unit 104 are inserted in opening 422 in the top of the inserter 406 so as to position the carrier 404 and electronics unit 104 within the inserter 406 (see FIG. 9A). The activator 402 is then moved relative to (e.g., within, in some embodiments) the carrier 404 causing the activator 402 to release the electronics unit 104 from the carrier 404 and couple the electronics unit 104 to the base unit 102 (see FIG. 9B).

The coupling tool 400 may be referred to as being in an unlocked configuration when the coupling tool 400 is configured to release the electronics unit 104. The coupling tool 400 may be referred to as being in a locked configuration when the coupling tool 400 is configured to retain the electronics unit 104.

Figure 5A:
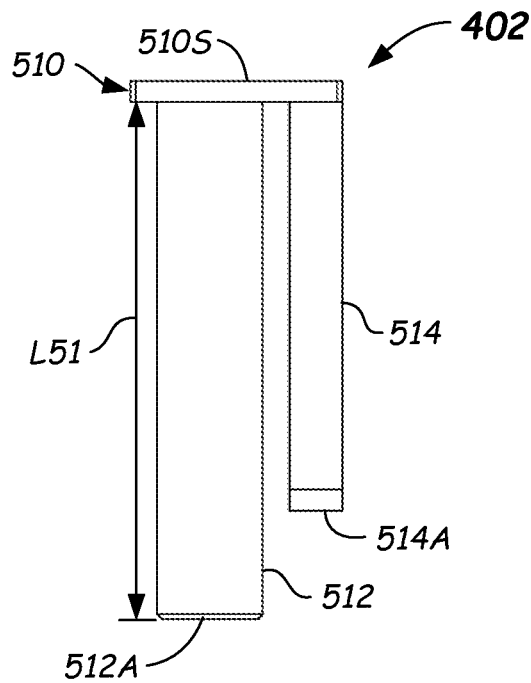
FIG. 5A illustrates a side elevation view of an activator of a coupling tool used to couple an electronics unit to a base unit of a wearable device for use during continuous analyte monitoring in accordance with embodiments provided herein.
Figure 5B:
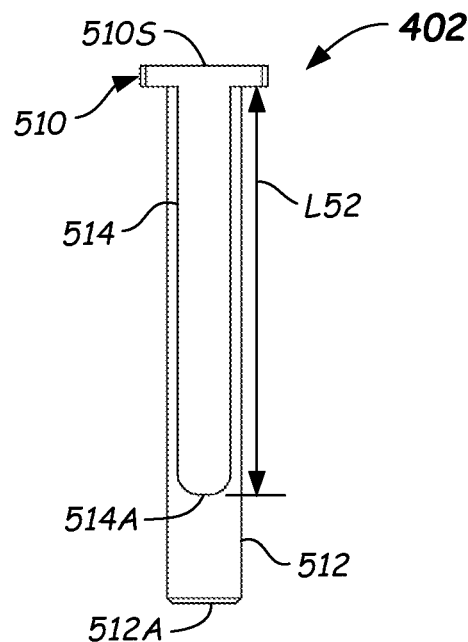
FIGS. 5B-5D illustrate a front elevation view, a top isometric view, and a bottom isometric view, respectively, of the activator of FIG. 5A in accordance with embodiments provided herein.
Figure 5C:
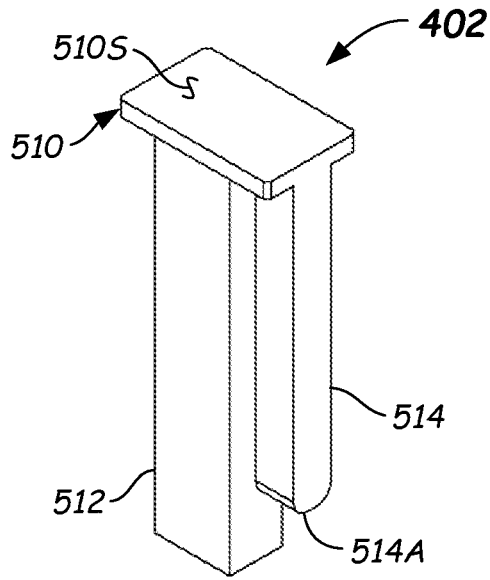
Figure 5D:
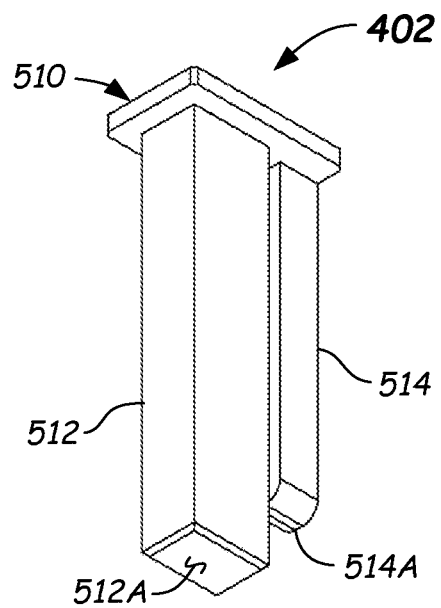

Additional reference is made to FIGS. 5A-5D, which illustrate various views of the activator 402 according to embodiments provided herein. FIG. 5A illustrates a side elevation view of the activator 402, FIG. 5B illustrates a front elevation view of the activator 402, FIG. 5C illustrates a top isometric view of the activator 402, and FIG. 5D illustrates a bottom isometric view of the activator 402. The activator 402 may include a top portion 510 having a top surface 510S. The top surface 510S may be configured to be pressed by a user during coupling of the electronics unit 104 to the base unit 102.

A first member 512 may extend a length L51 from the top portion 510 to an end 512A. The end 512A may be configured to contact the electronics unit 104 as the electronics unit 104 and the base unit 102 are coupled together. For example, the end 512A may be configured to contact the top cover 204 (FIG. 2) of the electronics unit 104. The first member 512 may be rigid enough to withstand forces applied between the electronics unit 104 and the base unit 102 during coupling. In some embodiments, the activator 402 may be referred to as being in a locked position or configuration when the end 512A does not contact the electronics unit 104 and in an unlocked position or configuration when the end 512A contacts the electronics unit 104. In the unlocked position, the electronics unit 104 is no longer retained. The length L51 may be long enough to push the electronics unit 104 from the carrier 404 when the activator 402 is in the unlocked position as described herein.

The activator 402 may also include a contact member 514 extending from the top portion 510. The contact member 514 may extend a length L52 between the top portion 510 and an end 514A of the contact member 514. As described herein, the contact member 514 may engage moveable or flexible members of the carrier 404 to release the electronics unit 104 from the carrier 404 when the activator 402 is in the unlocked configuration or as the carrier 404 transitions from the locked configuration to the unlocked configuration as described herein.

Figure 6A:
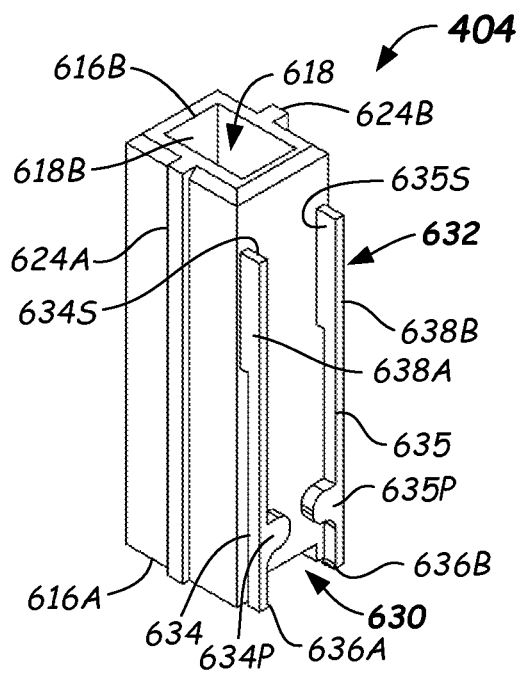
FIG. 6A illustrates a top isometric view of a carrier of a coupling tool used to couple an electronics unit to a base unit of a wearable device for use during continuous analyte monitoring in accordance with embodiments provided herein.
Figure 6B:
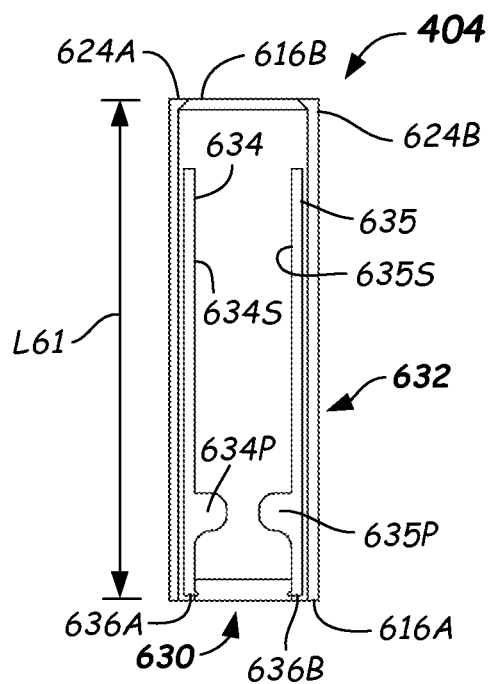
FIGS. 6B-6D illustrate a front elevation view, a bottom isometric view, and a side elevation view, respectively, of the carrier of FIG. 6A in accordance with embodiments provided herein.
Figure 6C:
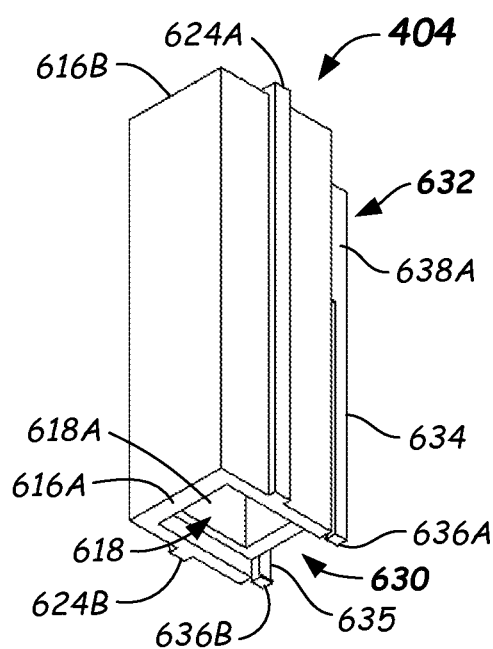
Figure 6D:
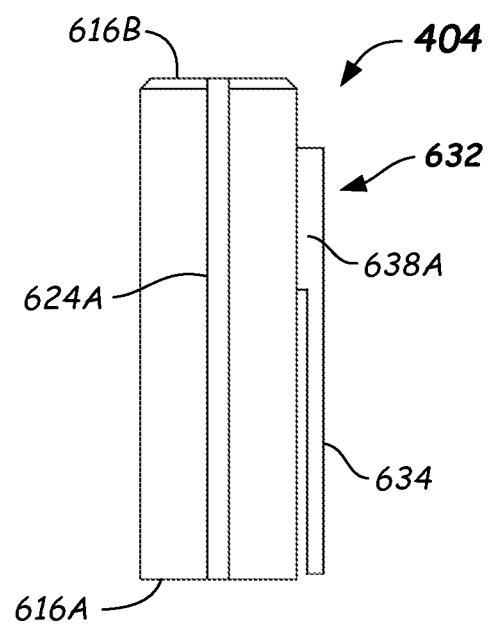

Additional reference is made to FIGS. 6A-6D, which illustrate different views of an embodiment of the carrier 404. FIG. 6A illustrates a top isometric view of the carrier 404, FIG. 6B illustrates a front elevation view of the carrier 404, FIG. 6C illustrates a bottom isometric view of the carrier 404, and FIG. 6D illustrates a side elevation view of the carrier 404.

The carrier 404 may be configured to carry the electronics unit 104 to the base unit 102 and/or the inserter 406. The carrier 404 may have a first side 616A (e.g., a bottom side) and a second side 616B (e.g., a top side). A length L61 extends between the first side 616A and the second side 616B. In some embodiments, the length L61 may be slightly less than the length L51 (FIG. 5A) of the first member 512 of the activator 402. The carrier 404 may have a receiving feature 618 (e.g., a rectangular hole as shown) extending between the first side 616A and the second side 616B. The receiving feature 618 may be shaped and/or sized to receive at least a portion of the first member 512 of the activator 402 and to enable the first member 512 to move (e.g., slide) within the receiving feature 618. The receiving feature 618 may comprise a receiving feature first end 618A and a receiving feature second end 618B, wherein the electronics unit 104 is configured to be positioned adjacent the receiving feature first end 618A when the coupling tool 400 is in the locked configuration, such as when the electronics unit 104 is retained by the carrier 404 (see FIGS. 7A-7B). The receiving feature 618 is shown as an aperture. In other embodiments, the receiving feature 618 may be a slot, a groove, or other feature that performs the functions described herein.

The carrier 404 may have an outer surface that defines a transverse shape of the carrier 404 when viewed from the first side 616A or the second side 616B. The transverse shape of the carrier 404 enables the carrier 404 to be received within an opening 422 (FIG. 4B) in the inserter 406 as described herein. For example, the carrier 404 may include a shape that is configured to allow the carrier 404 to slide within the opening 422. In some embodiments, the transverse shape of the carrier 404 may be the same as the opening 422, but slightly smaller to enable the carrier 404 to move with minimal friction within the opening 422.

Figure 4B:
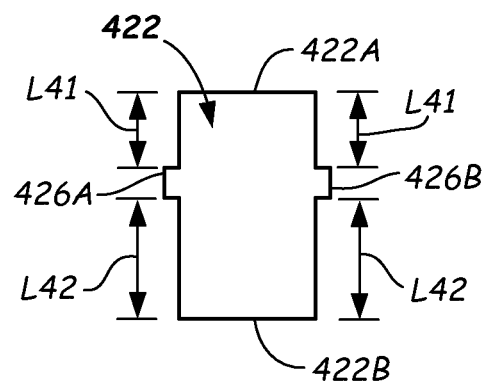
FIG. 4B illustrates a plan view of an opening in the inserter of FIG. 4A in accordance with embodiments provided herein.

Additional reference is made to FIG. 4B, which illustrates a plan view of the opening 422 in accordance with embodiments provided herein. The carrier 404 may include one or more indexing devices that orient the carrier 404 in a specific direction within the opening 422. In the embodiment of FIGS. 4B and 6A-6D, the carrier 404 includes two rails, a first rail 624A and a second rail 624B that extend from the outer surface and orient the carrier 404 within the opening 422. The first rail 624A and the second rail 624B may be receivable within a first channel 426A and a second channel 426B, respectively, of the opening 422. The locations of the first rail 624A, the second rail 624B, the first channel 426A, and the second channel 426B provide for the carrier 404 to be received in only one orientation within the opening 422. For example, in the embodiment of FIG. 4B, the opening 422 includes a first side 422A and an opposing second side 422B. Both the first channel 426A and the second channel may be located a length L41 from the first side 422A and a length L42 from the second side 422B, wherein the length L41 is not equal to the length L42. Accordingly, the locations of the first channel 426A and the second channel 426B enable the carrier 404 to be received in only one orientation within the opening 422. The one orientation provides for proper coupling of the electronics unit 104 and the base unit 102. Other indexing and/or orienting mechanisms may be used.

The carrier 404 is configured to retain the electronics unit 104 as shown in FIGS. 7A and 7B, which are bottom and top isometric views, respectively, of embodiments of the carrier 404 retaining the electronics unit 104 and with the activator 402 received therein. In some embodiments, the carrier 404 may have a cavity 630 (FIGS. 6A-C and 7C) configured (e.g., shaped and sized) to receive the electronics unit 104. The cavity 630 may be located proximate the first side 616A of the carrier 404 and may intersect with the receiving feature 618 (FIG. 6A), so that the end 512A (FIGS. 5A-5D) of the first member 512 of the activator 402 may contact the electronics unit 104. For example, the cavity 630 may be in or adjacent the receiving feature first end 618A of the receiving feature 618. The first member 512 of the activator 402 may contact the electronics unit 104 to force the electronics unit 104 and the base unit 102 together as shown in FIG. 9B. In some embodiments, the cavity 630 is configured to retain the electronics unit 104 flush with the first side 616A of the carrier 404.

In some embodiments, the carrier 404 may include one or more retention devices that are configured to retain the electronics unit 104 to the carrier 404, such as within the cavity 630 or otherwise at the end of carrier 404. The carrier 404 and/or the one or more retention devices may be in a locked configuration or a locked state when the carrier 404 retains or is configured to retain the electronics unit 104. The carrier 404 and/or the one or more retention devices may be in an unlocked configuration or an unlocked state when the electronics unit 104 is released from the carrier 404 or the carrier 404 is configured to release the electronics unit 104. In the embodiments of FIGS. 6A-7C, the carrier 404 may include a carrier retention device 632 that is configured to retain the electronics unit 104, such as within the cavity 630, and enables the contact member 514 (FIG. 4A) of the activator 402 to release the electronics unit 104 from the cavity 630. For example, the contact member 514 (FIGS. 5A-5D and 7A-7C) may be configured to release the electronics unit 104 from the carrier retention device 632 in response to movement of the activator 402 relative to the carrier 404.

The carrier retention device 632 may include one or more hooks that retain the electronics unit 104 to the carrier 404. In the embodiments of FIGS. 6A-7C, the carrier retention device 632 may include a first arm 634 having a first hook 636A and a second arm 635 having a second hook 636B. The first arm 634 may pivot about or be flexible about a first point 638A and the second arm 635 may pivot about or be flexible about a second point 638B. In some embodiments, the first point 638A and the second point 638B may be locations where the first arm 634 and the second arm 635 connect to a body portion of the carrier 404. In some embodiments, the first arm 634 and the second arm 635 are flexible such the first arm 634 and the second arm 635 flex upon interaction or engagement with the contact member 514 of the activator 402 as described herein to release the electronics unit 104 from the cavity 630. First arm 634 and the second arm 635 may be separated from the main body of the carrier 404 by a gap.

The first hook 636A and the second hook 636B may be configured to grasp and/or retain the electronics unit 104 to the carrier 404 when the carrier 404 is in the locked configuration. In some embodiments, the first hook 636A and the second hook 636B may be configured to engage two of the retention features (e.g., retention features 128A-D shown in FIG. 2) of the electronics unit 104 to retain the electronics unit 104 in the cavity 630. In the embodiment depicted in FIGS. 7A-7B, the first hook 636A is shown engaged with the retention feature 128C and the second hook 636B is shown engaged with the retention feature 128A, which retain the electronics unit 104 in the cavity 630.

The first arm 634 may have an inner surface 634S (FIG. 6B) and the second arm 635 may have an inner surface 635S that faces the inner surface 634S. The inner surface 634S and the inner surface 635S may guide the contact member 514 of the activator 402 between the first arm 634 and the second arm 635. The first arm 634 may also have a first protrusion 634P that includes a portion of the inner surface 634S. The second arm 635 may also have a second protrusion 635P that includes a portion of the inner surface 635S. The first protrusion 634P and the second protrusion 635P may be configured to be in contact with the contact member 514 as the activator 402 transitions to the unlocked configuration, which transitions the carrier 404 to the unlocked configuration and releases the electronics unit 104 as described herein.

When the activator 402 is in the locked configuration, the carrier 404 is in the locked configuration. In some embodiments, first arm 634 and the second arm 635 may be biased toward each other, so that the carrier 404 may normally be in the locked configuration. In some embodiments, the first hook 636A and the second hook 636B may be normally biased toward each other so that the carrier 404 is normally in the locked configuration. As the contact member 514 of the activator 402 engages the first protrusion 634P and the second protrusion 635P, the first hook 636A and the second hook 636B separate from each other, which places the carrier 404 in the unlocked configuration and releases the electronics unit 104 from the cavity 630. For example, the first arm 634 and the second arm 635 flex or pivot about the first point 638A and the second point 638B. Thus, the carrier 404 transitions to the unlocked configuration and the electronics unit 104 is released from the carrier 404. The location of the first protrusion 634P on the first arm 634 and the location of the second protrusion 635P on the second arm 635 determine the distance the contact member 514 is positioned within the carrier 404 when the activator 402 engages the carrier retention device 632 and transitions the carrier 404 between the locked configuration and the unlocked configuration.

As the contact member 514 of the activator 402 releases the electronics unit 104 from the carrier 404, the first member 512 of the activator 402 may eject the electronics unit 104 from the carrier 404. For example, the end 512A of the first member 512 may contact the electronics unit 104 and force the electronics unit 104 and the base unit 102 together. The length L51 of the first member 512 and the length L52 of the contact member 514 may provide for the carrier 404 to transition to the unlocked configuration just prior to the first member 512 ejecting the electronics unit 104 from the carrier 404. In some embodiments, the locations of the first protrusion 634P and the second protrusion 635P on the first arm 634 and the second arm 635 may also provide for the carrier 404 transitioning to the unlocked configuration prior to the first member 512 ejecting the electronics unit 104 from the carrier 404.

The electronics unit 104 may be retained in the carrier 404 by forcing the electronics unit 104 into the cavity 630. The force may flex the first arm 634 and the second arm 635 away from each other. As the electronics unit 104 is further pushed into the cavity 630, the first hook 636A and the second hook 636B may engage the second retention features 128 on the electronics unit 104 to retain the electronics unit 104 within the cavity 630.

In some embodiments, the inserter 406 may be a device that attaches the wearable device 100 to the skin of a user. For example, the inserter 406 may enable a user to attach the wearable device 100 to the skin and locate the analyte sensor 114 in a subcutaneous region. The wearable device 100 may be attached to the skin of the user prior to, during, or after coupling of the electronics unit 104 to the base unit 102.

Figure 8A:
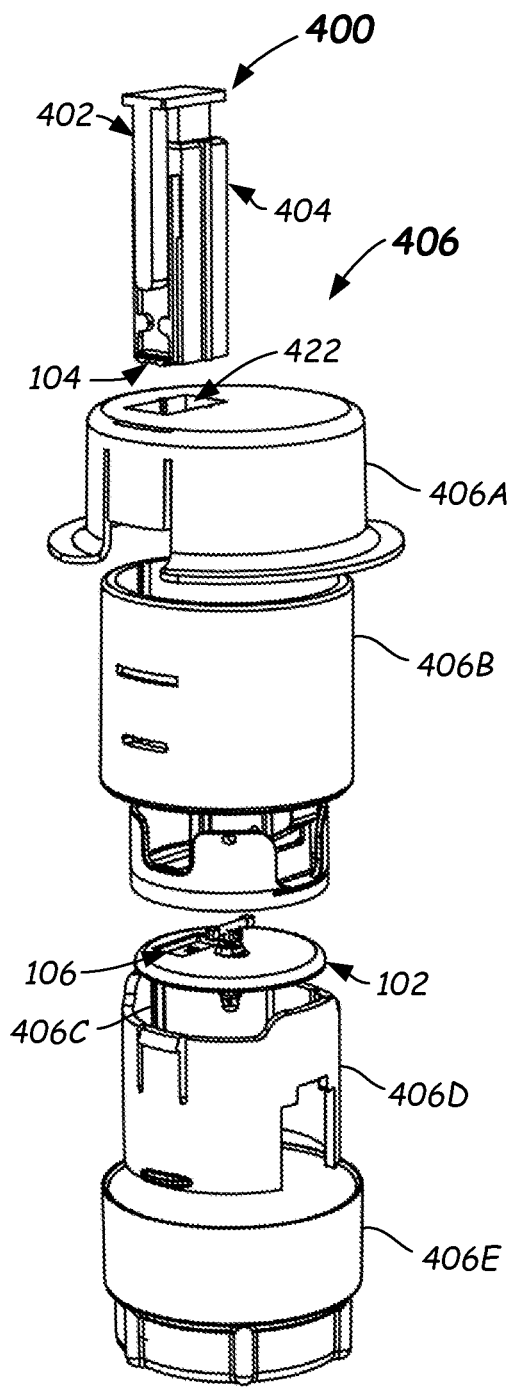
FIG. 8A illustrates an exploded isometric view of an inserter for a wearable device for use during continuous analyte monitoring and a coupling tool configured to couple an electronics unit to a base unit of the wearable device, wherein the coupling tool and electronics unit are received in the inserter in accordance with embodiments provided herein.
Figure 8B:
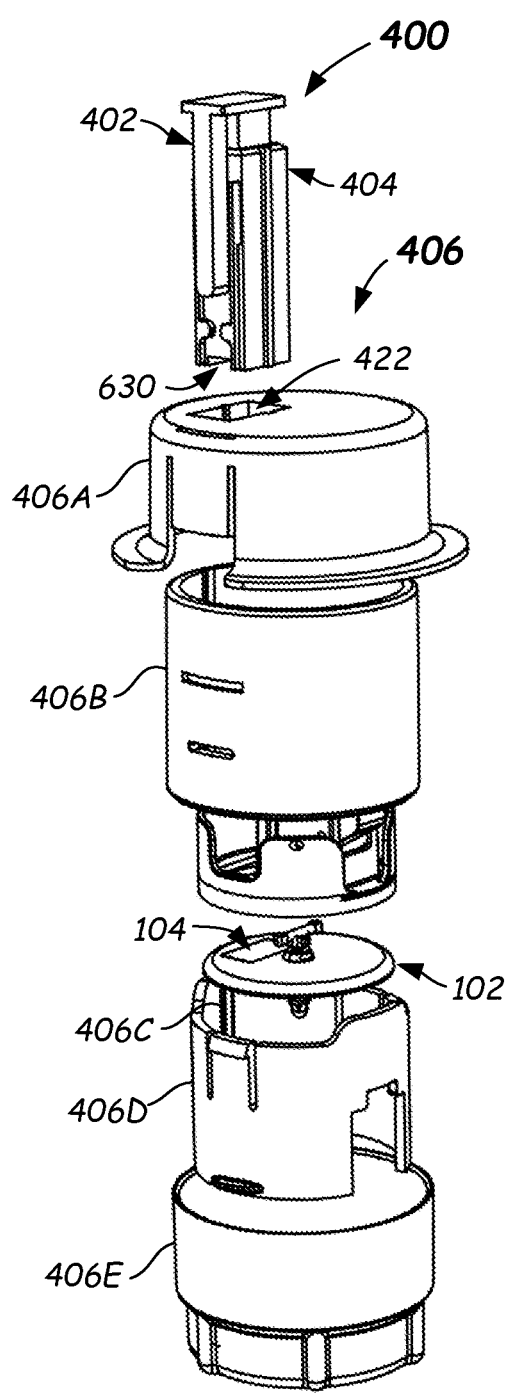
FIG. 8B illustrates an exploded isometric view of an inserter for a wearable device used during continuous analyte monitor and a coupling tool configured to couple an electronics unit to a base unit of the wearable device, wherein the electronics unit is received in the base unit and the coupling tool is retracted in accordance with embodiments provided herein.

Reference is now made to FIGS. 8A and 8B. FIG. 8A illustrates an exploded isometric view of an embodiment of the inserter 406 and the coupling tool 400 according to embodiments provided herein. In the embodiment of FIG. 8A, the electronics unit 104 is received in the coupling tool 400. FIG. 8B illustrates an exploded isometric view of an embodiment of the inserter 406 and the coupling tool 400 with the electronics unit 104 coupled to (e.g., received within) the base unit 102 according to embodiments provided herein. In the configuration depicted in FIG. 8A, the coupling tool 400 is in a locked configuration wherein the electronics unit 104 is retained by the carrier 404. The inserter 406 depicted herein is an example of one of many inserters that may be used with the coupling tool 400. The inserters used with the coupling tool 400 may have an opening 422 or the like that provides access for the coupling tool 400 to access an opening or the like on a base unit 102 that receives the electronics unit 104. In some embodiments, a support or other device that supports the base unit 102 during coupling of the base unit 102 and the electronics unit 104 may be used instead of the inserter 406.

The inserter 406 may include a top cover 406A that includes the opening 422. As described above, the coupling tool 400 is at least partially receivable in the opening 422. The inserter 406 may also include an outer sleeve 406B wherein the top cover 406A may slide over the outer sleeve 406B and couple thereto. In some embodiments, some portions of a mechanism (not shown in FIGS. 8A-8B) that insert the analyte sensor 114 (FIG. 1D) in a subcutaneous region of a user may be located within the outer sleeve 406B. The inserter 406 may include a base unit support 406C that may be at least partially receivable within an inner sleeve 406D. As shown, the base unit support 406C may be configured to support the base unit 102 during coupling of the electronics unit 104 to the base unit 102. In some embodiments, the inserter 406 may include a cap 406E that covers a lower portion of the inserter 406 and/or a lower portion of the base unit 102.

The opening 422 may provide an access between the top cover 406A and the opening 106 in the base unit 102 that receives the electronics unit 104. Thus, the opening 422 enables the coupling tool 400 with the electronics unit 104 attached thereto, as shown in FIG. 8A, to pass into the opening 422. The coupling tool 400 may then be used to couple the electronics unit 104 and the base unit 102 together as shown in FIG. 8B. In the example of FIG. 8B, the electronics unit 104 is inserted into the base unit 102. Similarly, base unit support 406C can have an opening that enables the coupling tool 400 with the electronics unit 104 attached thereto to pass through to couple the electronics unit 104 to the base unit 102.

Figure 9A:
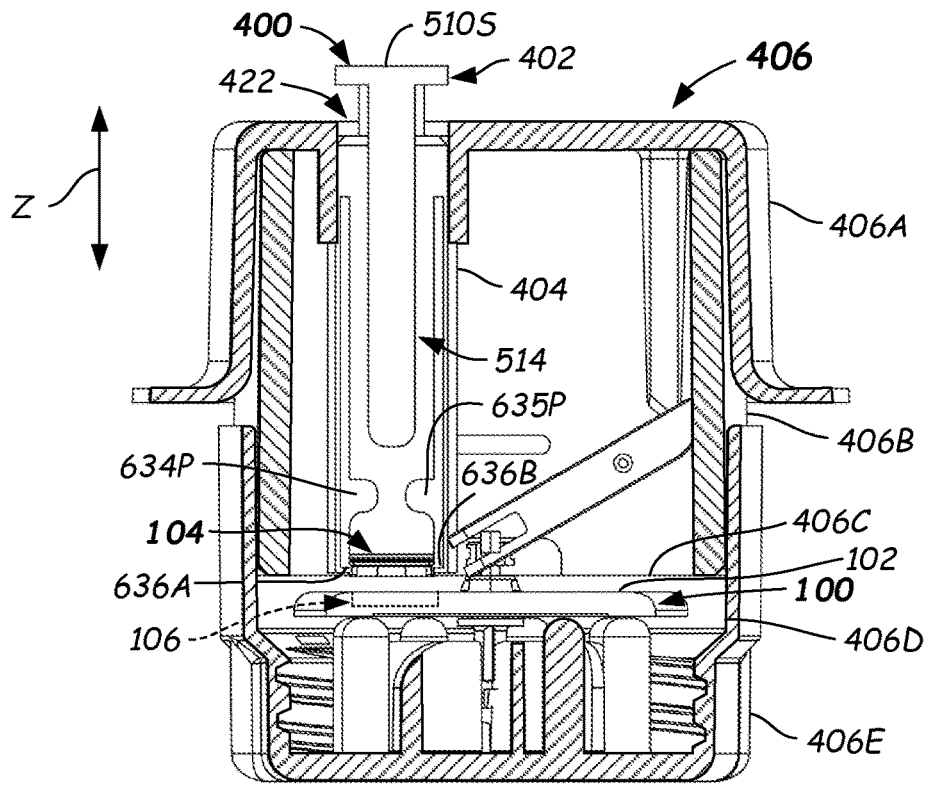
FIG. 9A illustrates a cross-sectioned side view of the inserter of FIG. 8A including the coupling tool in a locked configuration, wherein the electronics unit is retained by the coupling tool in accordance with embodiments provided herein.
Figure 9B:
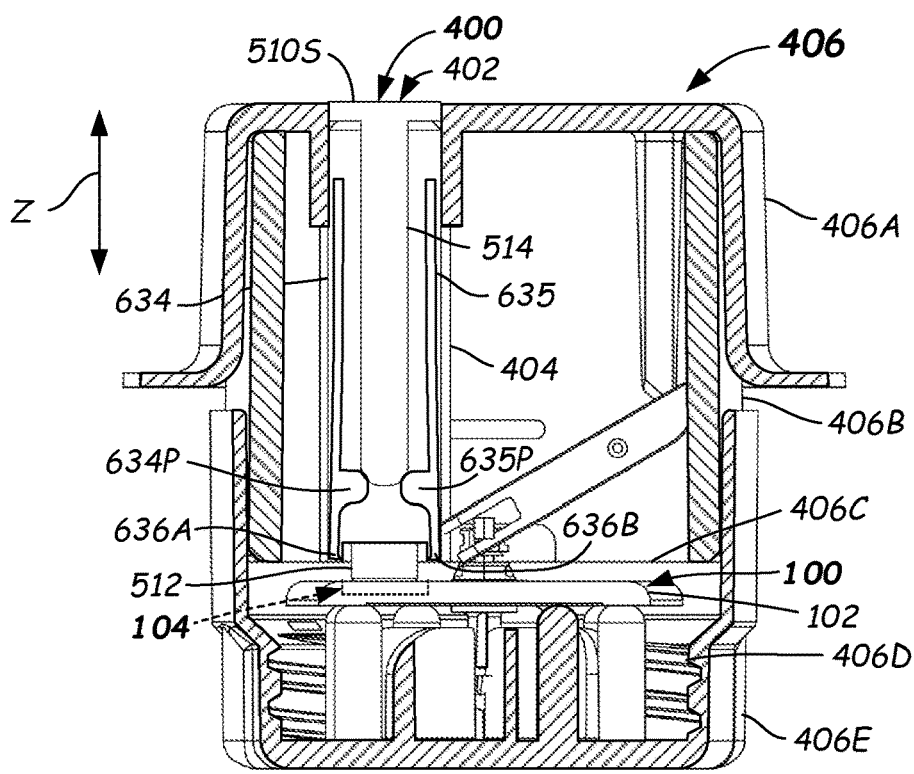
FIG. 9B illustrates a cross-sectioned side view of the inserter of FIG. 9A with the coupling tool in an unlocked configuration and the electronics unit and base unit coupled together in accordance with embodiments provided herein.

Reference is now made to FIGS. 9A and 9B, which illustrate partial cross-sectioned views of the inserter 406 with the base unit 102, electronics unit 104, and coupling tool 400 located therein. In the configuration of FIG. 9A, the coupling tool 400 is in the locked configuration and the electronics unit 104 is retained by the coupling tool 400. In the configuration of FIG. 9B, the coupling tool 400 is in the unlocked configuration and the electronics unit 104 has been coupled with the base unit 102. For example, the electronics unit 104 has been inserted into the base unit 102.

In the configuration of FIG. 9A, the coupling tool 400 is located at least partially in the opening 422 and is in the locked configuration. As shown in FIG. 9A, the activator 402 is not fully inserted into the carrier 404, so the contact member 514 is not contacting either the first protrusion 634P or the second protrusion 635P. Accordingly, the coupling tool 400 is in the locked configuration with the electronics unit 104 retained thereto.

In the configuration of FIG. 9B, the coupling tool 400 has been used to insert the electronics unit 104 into the base unit 102. As shown in FIG. 9B, the activator 402 has been pressed in the z-direction into the carrier 404, which has caused the contact member 514 to contact the first protrusion 634P and the second protrusion 635P. The contact with the first protrusion 634P and the second protrusion 635P causes the first hook 636A and the second hook 636B to move away from each other, which releases the electronics unit 104 from the carrier 404. As the activator 402 is pressed further into the carrier 404, the end 512S (FIGS. 5A-5D) of the first member 512 contacts the electronics unit 104 and forces the electronics unit 104 into the opening 106 in the base unit 102. When the electronics unit 104 is coupled to the base unit 102, a waterproof seal may be formed between the base unit 102 and the electronics unit 104 that prevents contaminants from entering the opening 106.

As the electronics unit 104 and the base unit 102 are coupled together, the second retention features 128 (FIG. 1F) of the electronics unit 104 engage with the first retention features 126 of the base unit 102 and couple the electronics unit 104 and the base unit 102 together. After the electronics unit 104 and the base unit 102 are coupled together, the coupling tool 400 may be removed from the inserter 406, and the wearable device 100, including the electronics unit 104 and the base unit 102, may be applied (e.g., attached or adhered) to a user. In some embodiments, the coupling tool 400 may be used to couple the electronics unit 104 and the base unit 102 together after the base unit 102 has been applied to a user.

The wearable device 100 (FIG. 1A) may be worn by a user for a period, such as two weeks or such time as the base unit 102 needs to be replaced and/or removed from the user. During this period, the wearable device 100 may be monitoring/measuring analytes, such as in a subcutaneous region of the user. Following analyte monitoring, the wearable device 100 may be detached from the user. The electronics unit 104 of the wearable device 100 may then be disconnected/decoupled from the base unit 102. For example, the electronics unit 104 may be decoupled from the base unit 102 and the base unit 102 may be discarded. In general, the electronics unit 104 may be decoupled from the base unit 102 before or after the base unit 102 is removed from the user. Thereafter, the electronics unit 104 may be coupled to a new base unit using the coupling tool 400 as described herein. The new base unit may include a new power source and a new analyte sensor.

Figure 10:
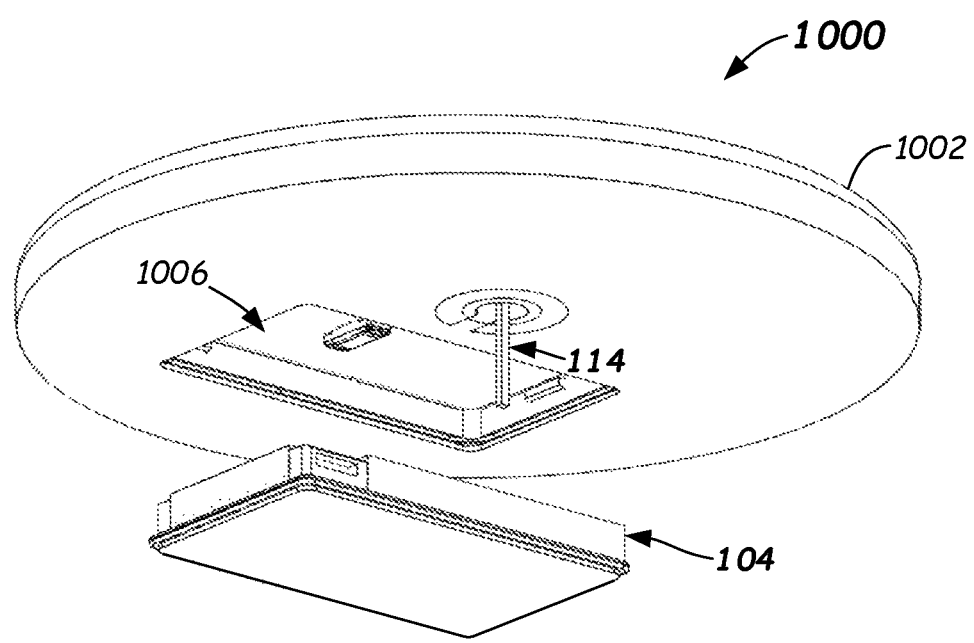
FIG. 10 illustrates a bottom isometric view of another example of a wearable device for use in continuous analyte monitoring showing the relationship between an electronics unit and a base unit in accordance with embodiments provided herein.

While the electronics unit 104 is shown as being coupled to the top surface of the base unit 102, it will be understood that in other embodiments, electronics unit 104 may be removable and/or coupled to other surfaces of a base unit. For example, FIG. 10 illustrates a bottom view of a base unit 1002 of a wearable device 1000 having an opening 1006 that allows the electronics unit 104 and the base unit 1002 to be coupled together using the coupling tool 400 (FIG. 4) in accordance with embodiments described herein. In some embodiments, the base unit 1002 may be placed in a device other than an inserter that enables the coupling tool 400 to access the opening 1006.

Figure 11:
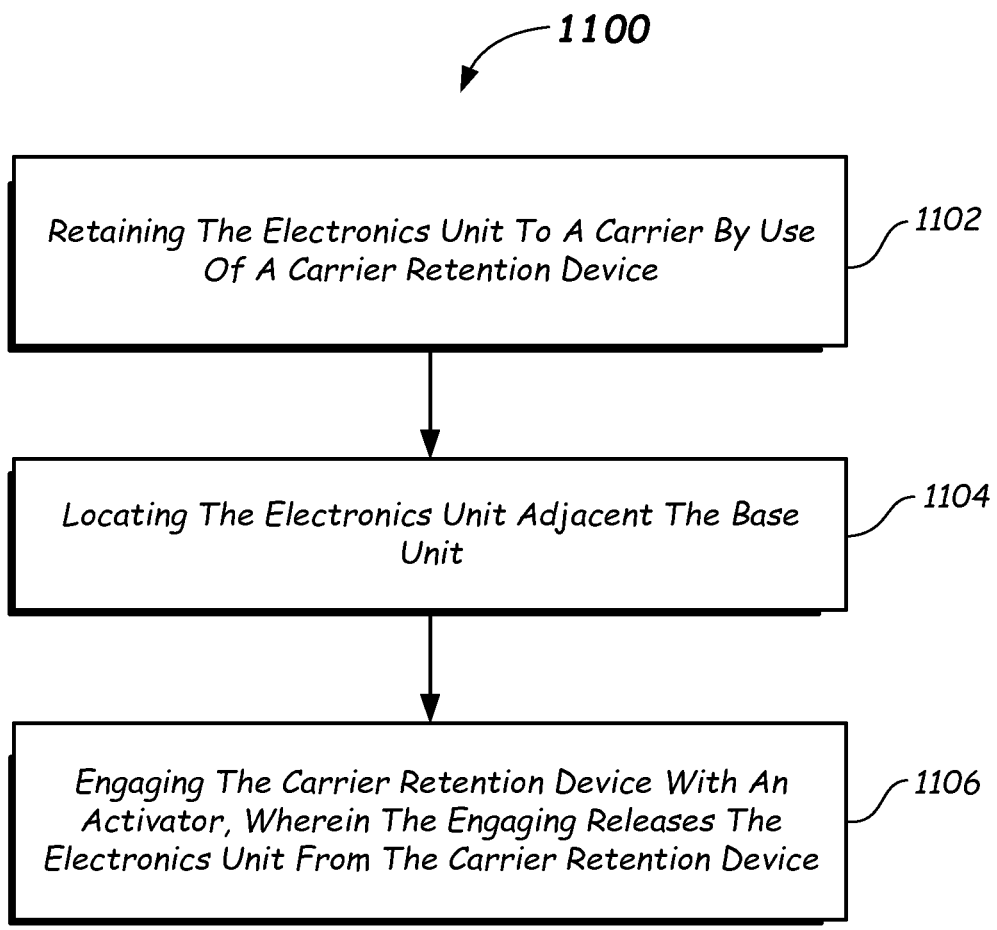
FIG. 11 illustrates a flowchart of an example method of coupling an electronics unit to a base unit of a wearable device for use in continuous analyte monitoring device in accordance with embodiments provided herein.

Reference is now made to FIG. 11, which is a flowchart depicting an example of a method 1100 of coupling together an electronics unit (e.g., electronics unit 104) and a base unit (e.g., base unit 102) of a wearable device (e.g., wearable device 100) for using during continuous analyte monitoring. The method 1100 includes, at process block 1102, retaining the electronics unit to a carrier (e.g., carrier 404), by use of a carrier retention device (e.g., carrier retention device 632). The method 1100 also includes, at process block 1104, positioning the electronics unit adjacent the base unit. The method further includes, at process block 1106, engaging the carrier retention device with an activator (e.g., activator 402), wherein the engaging releases the electronics unit from the carrier retention device. Further motion of the activator couples the electronics unit to the base unit.

The foregoing description discloses only example embodiments. Modifications of the above-disclosed apparatus and methods which fall within the scope of this disclosure will be readily apparent to those of ordinary skill in the art.

What is claimed is:

1. A system comprising:
   a coupling tool for coupling together an electronics unit and a base unit of a wearable device for continuous analyte monitoring, the coupling tool comprising:
   a carrier comprising a receiving feature and a carrier retention device, the carrier retention device configured to engage the electronics unit to retain the electronics unit adjacent the receiving feature; and
   an activator comprising:
   a first member comprising a first portion at least partially receivable in the receiving feature and a first end configured to contact the electronics unit to thereby couple the electronics unit to the base unit;
   a contact member comprising a second portion and a second end configured to contact at least a portion of the carrier retention device in response to movement of the activator relative to the carrier to thereby release the electronics unit from the carrier retention device; and
   a top portion directly attached to the first member and the contact member and configured to be pressed by a user during coupling of the electronics unit to the base unit,
   wherein the first portion of the first member extends a first length from the top portion to the first end and the second portion of the contact member extends a second length from the top portion to the second end,
   wherein the coupling tool is in a locked configuration when the carrier retention device is configured to retain the electronics unit,
   wherein the coupling tool is in an unlocked configuration when the carrier retention device is configured to release the electronics unit from the carrier retention device.

2. The system of claim 1, wherein the carrier retention device comprise one or more hooks configured to retain the electronics unit when the coupling tool is in the locked configuration.

3. The system of claim 1, wherein the receiving feature comprises a receiving feature first end and a receiving feature second end, and the electronics unit is configured to be located adjacent the receiving feature first end when the coupling tool is in the locked configuration.

4. The system of claim 1, wherein the carrier retention device comprises a first arm and a second arm configured to retain the electronics unit in response to the coupling tool being in the locked configuration and configured to be contacted by the second end of the contact member in response to the coupling tool being in the unlocked configuration.

5. The system of claim 4, wherein the first arm and the second arm are flexible such that the first arm and the second arm can flex to release the electronics unit in response to the coupling tool being in the unlocked configuration.

6. The system of claim 1, further comprising:
   an inserter configured to attach the base unit to the user, wherein the coupling tool is configured to be received within the inserter.

7. The system of claim 6, wherein the inserter comprises a base unit support configured to support the base unit within the inserter.

8. The system of claim 1,
   wherein the first length is larger than the second length such that the carrier transitions to the unlocked configuration prior to contacting the electronics unit with the first member.

9. The system of claim 1, wherein the receiving feature comprises a hole extending through the carrier and operable to receive at least a portion of the first member.

10. A method of coupling an electronics unit to a base unit of a wearable device of a continuous analyte monitoring system, comprising:
    retaining the electronics unit to a carrier of a coupling tool by use of a carrier retention device;
    positioning the electronics unit adjacent the base unit;
    engaging the carrier retention device with an activator of the coupling tool, the activator comprising a first member comprising a first portion and a first end configured to contact the electronics unit, a contact member comprising a second portion and a second end configured to contact at least a portion of the carrier retention device, and a top portion directly attached to the first member and the contact member, wherein the first portion of the first member extends a first length from the top portion to the first end and the second portion of the contact member extends a second length from the top portion to the second end, wherein the engaging the carrier retention device with the activator includes contacting the at least a portion of the carrier retention device with the second end of the contact member to release the electronics unit from the carrier retention device; and coupling the electronics unit to the base unit by contacting the electronics unit with the first end of the first member, wherein the top portion is configured to be pressed by a user during the coupling of the electronics unit to the base unit.

11. The method of claim 10, wherein the carrier retention device comprises a first arm and a second arm configured to retain the electronics unit and the engaging the carrier retention device with the activator comprises contacting at least one of the first arm or the second arm with the activator to release the electronics unit from the carrier retention device.

12. The method of claim 11, wherein the contacting at least one of the first arm or the second arm with the activator comprises contacting at least one of the first arm or the second arm with the second end of the contact member to release the electronics unit from the carrier retention device.

13. The method of claim 12, wherein the first arm and the second arm are flexible and the contacting at least one of the first arm or the second arm with the contact member comprises flexing at least one of the first arm or the second arm using the contact member, wherein the flexing releases the electronics unit from the carrier retention device.

14. The method of claim 10,
wherein the carrier comprises a receiving feature operable to receive at least a portion of the first member,
wherein the retaining the electronics unit to the carrier comprises retaining the electronics unit adjacent the receiving feature.

15. The method of claim 10, further comprising:
locating the base unit in an inserter configured to attach the base unit to the user; and
receiving at least a portion of the carrier in the inserter.

16. The method of claim 10, wherein the releasing the electronics unit from the carrier retention device occurs prior to coupling the electronics unit to the base unit.

17. A coupling tool, comprising:
a carrier comprising a receiving feature;
a carrier retention device attached to the carrier, the carrier retention device comprising a first arm and a second arm configured to retain an electronics unit adjacent the receiving feature; and
an activator comprising:
a first member comprising a first portion at least partially receivable in the receiving feature and a first end configured to contact the electronics unit to couple the electronics unit to a base unit of a wearable device of a continuous analyte monitor in response to the coupling tool being in an unlocked configuration;
a contact member comprising a second portion and a second end configured to contact at least a portion of the carrier retention device in response to the coupling tool being in the unlocked configuration to thereby release the electronics unit from the carrier retention device; and
a top portion directly attached to the first member and the contact member and configured to be pressed by a user during coupling of the electronics unit to the base unit,
wherein the first portion of the first member extends a first length from the top portion to the first end and the second portion of the contact member extends a second length from the top portion to the second end,
wherein the first portion of the first member and the second portion of the contact member extend parallelly from the top portion.

18. The coupling tool of claim 17, wherein the first arm and the second arm are flexible and configured to flex upon interaction with the second end of the contact member such that the electronics unit is released from the carrier retention device.

19. The coupling tool of claim 17,
wherein the first length and the second length cause the carrier to transition to the unlocked configuration prior to contacting the electronics unit with the first member.

20. The coupling tool of claim 17,
wherein the carrier further comprises a first side and a second side,
wherein the receiving feature comprises an aperture extending between the first side and the second side,
wherein the electronics unit is configured to be located adjacent the first side when the coupling tool is in a locked configuration.

* * * * *